US011432932B2

(12) United States Patent
Hwa

(10) Patent No.: US 11,432,932 B2
(45) Date of Patent: Sep. 6, 2022

(54) KNEE JOINT PROSTHESIS AND TIBIAL COMPONENT THEREOF

(71) Applicants: Su-Yang Hwa, Taipei (TW); INNOLUX CORPORATION, Jhu-Nan (TW)

(72) Inventor: Su-Yang Hwa, Taipei (TW)

(73) Assignees: Su-Yang Hwa, Taipei (TW); INNOLUX CORPORATION, JJhu-Nan (TW)

(*) Notice: Subject to any disclaimer, the term of this patent is extended or adjusted under 35 U.S.C. 154(b) by 308 days.

(21) Appl. No.: 16/366,608

(22) Filed: Mar. 27, 2019

(65) Prior Publication Data

US 2019/0216609 A1 Jul. 18, 2019

Related U.S. Application Data

(63) Continuation of application No. 15/012,328, filed on Feb. 1, 2016, now abandoned.

(30) Foreign Application Priority Data

Feb. 13, 2015 (TW) .................................. 104105153
Jan. 14, 2016 (CN) .......................... 201610023838.1

(51) Int. Cl.
*A61F 2/38* (2006.01)
*A61F 2/30* (2006.01)

(52) U.S. Cl.
CPC .............. *A61F 2/3868* (2013.01); *A61F 2/38* (2013.01); *A61F 2/389* (2013.01); *A61F 2/3859* (2013.01);
(Continued)

(58) Field of Classification Search
CPC ....................................................... A61F 2/389
See application file for complete search history.

(56) References Cited

U.S. PATENT DOCUMENTS 3,869,731 A   3/1975 Waugh et al.
4,759,767 A   7/1988 Lacey
(Continued)

FOREIGN PATENT DOCUMENTS

DE   3429157 A1   2/1986
DE   9416881 U    12/1994
(Continued)

OTHER PUBLICATIONS

Translation of DE29701082U1 retrieved from Espacenet on Mar. 23, 2021 (Year: 2021).*
(Continued)

*Primary Examiner* — Megan Y Wolf
(74) *Attorney, Agent, or Firm* — Muncy, Geissler, Olds & Lowe, P.C.

(57) ABSTRACT

The knee joint prosthesis includes a tibial component and a femoral component. The tibial component has a top surface, a bottom surface opposite to the top surface and a first slot passing through the top surface and the bottom surface for accommodating a cruciate ligament. The tibial component has at least one first protrusion disposed on the bottom surface, and the first protrusion has a plurality of first through holes. The femoral component is carried by the tibial component and has a second slot for accommodating the cruciate ligament. The femoral component has at least one second protrusion disposed on a surface thereof opposite to the tibial component, and the second protrusion has a plurality of second through holes. The first protrusion has a first rear and front portions, and a width of the first protrusion gradually becomes thicker from the first rear portion toward the first front portion.

18 Claims, 20 Drawing Sheets

(52) U.S. Cl.
CPC ............... *A61F 2002/30884* (2013.01); *A61F 2002/30891* (2013.01); *A61F 2002/30892* (2013.01); *A61F 2002/30899* (2013.01); *A61F 2002/30902* (2013.01)

(56) References Cited

U.S. PATENT DOCUMENTS

| | | | |
|---|---|---|---|
| 4,963,153 | A | 10/1990 | Noesberger et al. |
| 4,978,357 | A | 12/1990 | Goymann et al. |
| 5,137,536 | A | 8/1992 | Koshino |
| 5,609,645 | A | 3/1997 | Vinciguerra |
| 6,258,127 | B1 | 7/2001 | Schmotzer |
| 2005/0112397 | A1 | 5/2005 | Rolfe et al. |
| 2005/0124998 | A1* | 6/2005 | Coon ................ A61F 2/461 606/99 |
| 2006/0116772 | A1 | 6/2006 | Haidukewych |
| 2006/0122705 | A1 | 6/2006 | Morgan |
| 2006/0212124 | A1 | 9/2006 | Siebel |
| 2007/0088442 | A1 | 4/2007 | Cima et al. |
| 2007/0173858 | A1 | 7/2007 | Engh et al. |
| 2008/0133020 | A1 | 6/2008 | Blackwell et al. |
| 2009/0130167 | A1 | 5/2009 | Shelton et al. |
| 2009/0228114 | A1 | 9/2009 | Clark et al. |
| 2010/0249941 | A1* | 9/2010 | Fell ..................... A61F 2/389 623/20.28 |
| 2010/0256758 | A1 | 10/2010 | Gordon et al. |
| 2011/0035017 | A1 | 2/2011 | Deffenbaugh et al. |
| 2011/0190898 | A1 | 8/2011 | Lenz et al. |
| 2014/0277549 | A1 | 9/2014 | Ell |
| 2016/0008136 | A1 | 1/2016 | Jones et al. |

FOREIGN PATENT DOCUMENTS

| | | | | |
|---|---|---|---|---|
| DE | 29701082 U1 | * | 5/1998 | ........... A61F 2/3662 |
| EP | 0860147 A2 | | 8/1998 | |

OTHER PUBLICATIONS

Definition of "to" retrieved from https://www.dictionary.com/browse/to on Sep. 2, 2021. (Year: 2021).*

* cited by examiner (a)

(b)

(c)

(d)

KNEE JOINT PROSTHESIS AND TIBIAL COMPONENT THEREOF

CROSS REFERENCE TO RELATED APPLICATIONS

This application is a Continuation Application (CA) of an earlier filed, pending, application, having application Ser. No. 15/012,328 and filed on Feb. 1, 2016, the content of which, including drawings, is expressly incorporated by reference herein.

BACKGROUND

Technical Field

The invention relates to a joint prosthesis, in particular to a knee joint prosthesis.

Related Art

Knee is the biggest human joint. It sustains a person's weight and lets the leg finely exercise flexion and extension. It includes the femoral condyles of the femur distal end, the tibial plateau of the tibia proximal end, the ligament (for example, the anterior cruciate ligament, the posterior cruciate ligament, the medial ligament and the lateral ligament, etc.), and the joint cartilage and meniscus. However, development defects of lower limb joints, bad standing, excessive exercises or ageing usually cause wears of joint cartilage and meniscus, so the lubricating fluid of knee articular capsule becomes less resulting in knee pain, swelling, difficult squat or other exercise impediment for example degenerative knee joint disease. More serious, it causes bowleg and the patient walks difficultly.

Total keen joint replacement is the most effective treatment for the symptom, it effectively alleviates pain due to arthritis and deformed joint and improves exercise range of the joint after implanting the knee joint prosthesis. But it still has some disadvantages.

A conventional knee joint prosthesis for total keen joint replacement is shown in FIG. 9A and FIG. 9B. The knee joint prosthesis includes a femoral implant a and a tibia assembly b. The tibia assembly b includes a tibial plate b1, a joint liner b2 and a tibial implant portion b3. The femoral implant a is nailed into the femoral condyles of the femur Fe by a femoral nail a2, and the tibia assembly b is fixed to the tibial plateau in the human body by the tibial implant portion b3 implanted into the tibia T. The central protrusion b22 of the joint liner b2 and the indentation a3 of the femoral implant a are disposed and limited correspondingly, so that the abutting surface a1 of the femoral implant a which faces the tibia T abuts the carry surface b21 of the joint liner b2 to rotate relatively, and the lower limb of the patient can exercise flexion and extension.

However, due to the life time of the knee joint prosthesis, the joint liner b2 substituting the knee meniscus suffers from the friction cause by the abutting surface a1 of the femoral implant a, thus it is damaged and incapable to use. Such the conventional knee joint prosthesis should be replaced over 15-20 years.

Besides, when the patient's knee exercises at an excessively angle or very intensively, the central protrusion b22 on the joint liner b2 may wear overly or may depart from the indentation a3 of the femoral implant a which causes dislocation. Even the central protrusion b22 on the joint liner b2 is severed by side intensive strike or rotation of the femoral implant a. In such situation, the knee joint prosthesis should be replaced.

In the above situation that the knee joint prosthesis should be replaced, because the original tibial implant portion b3 or the original femoral nail a2 has respectively damaged the tibia proximal end or the femur distal end overly, when implanting a new femoral implant a or tibia assembly b, it is necessary to thwack an additional long bone peg on the longitudinal direction of the femur Fe or the tibia T so the femoral implant a or the tibia assembly b are not loosen and stably disposed in the femur Fe or the tibia T. However, such thwacking an additional long bone peg will cause extra damage on the patient's bone. Even it is necessary to thwack a longer bone peg to keep the femoral implant a stable in the femur Fe or the tibia assembly b stable in the tibia T when implanting new femoral implant a or the tibia assembly b, so it causes more serious damage. Therefore, it is an unsolved problem in the field to dispose the joint prosthesis component stably on the implanted portion without using bone peg.

Besides, when the femoral condyles or the tibial plateau are respectively implanted into the femoral implant a or the tibia assembly b, the orthopedic surgeons generally applies a layer of bone cement (or biological glue) to the contact surface of the femoral implant a and the femoral condyles or the contact surface of the tibia assembly b and the tibial plateau to increase the stability of the femoral implant a or the tibia assembly b. However, before solidified, the bone cement easily enters systemic circulation from the artery of the injured area due to surgery. It may cause the skin or muscle tissue at the affected area necrosis, more seriously, it may cause the patient death due to myocardial infarction. Therefore, it is also an unsolved problem to keep considerable stability of the implanted knee joint prosthesis when decreasing the usage of the bond cement.

Furthermore, when utilizing the conventional knee joint prosthesis as shown in FIG. 9A and FIG. 9B to perform total keen joint replacement, it is necessary to resect the anterior cruciate ligament and the posterior cruciate ligament of the patient. Accordingly, the relative action between the femoral implant a and the tibia assembly b only relies on the indentation a3 of the femoral implant a and the fit of the central protrusion b22 correspondingly disposed on the joint liner b2. Thus, the stability of the patient's postoperative knee is insufficient, and the patient's postoperative knee cannot bend at too large angle. Therefore, it is also an unsolved problem to provide a knee joint prosthesis adapted to cruciate ligament-retaining when performing total keen joint replacement so as to retain the anterior cruciate ligament and the posterior cruciate ligament of the patient.

SUMMARY

A knee joint prosthesis includes a tibial component and a femoral component. The tibial component has a top surface, a bottom surface opposite to the top surface and a first slot passing through the top surface and the bottom surface for accommodating a cruciate ligament. The tibial component has at least one first protrusion disposed on the bottom surface, and the first protrusion has a plurality of first through holes. The femoral component is carried by the tibial component and has a second slot for accommodating the cruciate ligament. The femoral component has at least one second protrusion disposed on a surface thereof against the tibial component, and the second protrusion has a plurality of second through holes.

In one embodiment, the tibial component includes at least one sidewall and an engagement groove, and the sidewall surrounds the first slot and the engagement groove is disposed on the sidewall.

In one embodiment, the first protrusion has a first cutting edge and a first base, the first base is disposed between the first cutting edge and the bottom surface of the tibial component, and the first cutting edge gradually becomes thinner along the extending direction thereof.

In one embodiment, the tibial component has a through hole which does not overlap with the first base.

In one embodiment, the tibial component has a first side wall having a plurality of first apertures.

In one embodiment, the femoral component has two holding notches respectively located at two sides thereof.

In one embodiment, the second protrusion has a second cutting edge and a second base, the second base is disposed between the second cutting edge and the surface of the femoral component away from the tibial component, and the second cutting edge gradually becomes thinner along the extending direction thereof.

In one embodiment, the second protrusion has at least one position pillar, and the position pillar is disposed on the middle segment of the second protrusion.

In one embodiment, the knee joint prosthesis further comprises at least one pad. The pad is located between the tibial component and the femoral component.

In one embodiment, the pad has a second side wall, the second side wall has a plurality of second apertures.

In one embodiment, the pad has an abrasion meter.

A tibial component comprises a top surface, a bottom surface opposite the top surface and a first slot passing through the top surface and the bottom surface for accommodating a cruciate ligament. The tibial component has at least one protrusion disposed on the bottom surface and the protrusions has a plurality of through holes.

In one embodiment, the tibial component has at least one sidewall and an engagement groove, and the sidewall surrounds the slot and the engagement groove is disposed on the sidewall.

In one embodiment, the first protrusion has a first cutting edge and a first base, the first base is disposed between the first cutting edge and the bottom surface of the tibial component, the first cutting edge gradually becomes thinner along the extending direction thereof.

In one embodiment, the tibial component has a through hole which does not overlap with the first base.

In one embodiment, the tibial component has a first side wall, the first side wall has a plurality of first apertures.

A femoral component is disposed corresponding to a tibial component. The tibial component carries the femoral component. The femoral component includes a slot for accommodating a cruciate ligament. The femoral component has at least one protrusion on a surface thereof against the tibial component, and the protrusion has a plurality of through holes.

In one embodiment, the femoral component comprises two holding notches respectively located at two sides thereof.

In one embodiment, the protrusion has a cutting edge and a base, the base is disposed between the cutting edge and the surface of the femoral component away from the tibial component, and the cutting edge gradually becomes thinner along the extending direction thereof.

In one embodiment, the protrusion has at least one position pillar, the position pillar is disposed on the middle segment of the protrusion.

As mentioned above, as to the knee joint prosthesis, the tibial component and the femoral component thereof, because the tibial component and the femoral component respectively have at least one first protrusion and at least one second protrusion, and each of the first protrusion and the second protrusion respectively has at least one first through hole and at least one second through hole. After the tibial component and the femoral component are respectively implanted into the tibial plateau and the femoral condyles, the first protrusion is inserted into the tibial plateau and the second protrusion is inserted into the femoral condyles. The bone trabeculae in postoperative healing process will grow to pass through the first through hole and the second through hole so as to fix the tibial component and the femoral component to the implanted portion. Moreover, if the knee joint prosthesis is needed to replace in the future, the bone trabeculae can grow in the first through hole and the second through hole to fix the replaced tibial component or femoral component.

In addition to the above effect of the knee joint prosthesis and the tibial component and the femoral component thereof, in one embodiment, because the tibial component and the femoral component respectively have the first slot and the second slot disposed corresponding to each other for accommodating the cruciate ligament of the patient's knee, the orthopedic surgeons can adopt cruciate ligament-retaining to keep the stability of the postoperative joint and reduce the wear of the new joint when performs total keen joint replacement.

BRIEF DESCRIPTION OF THE DRAWINGS

The embodiments will become more fully understood from the detailed description and accompanying drawings, which are given for illustration only, and thus are not limitative of the present invention, and wherein.

DETAILED DESCRIPTION OF THE INVENTION

The embodiments of the invention will be apparent from the following detailed description, which proceeds with reference to the accompanying drawings, wherein the same references relate to the same elements. Moreover, the terms proximal, distal, anterior, posterior, medial, or lateral, etc. in the following embodiments are defined according to anatomy posture and indicative direction. Namely, "proximal" refers to facing the head, "distal" refers to facing the foot; "anterior" refers to facing the ventral of the body, "posterior" refers to facing to the dorsal of the body; "medial" refers to facing the central line of the body, "lateral" refers to departing from the central line of the body. Although the following embodiments take human knee for example, they are not limited thereto. Namely, the knee joint prosthesis of the following embodiments could be applied to other animal knee which has the same or similar anatomical structure.

Figure 1:
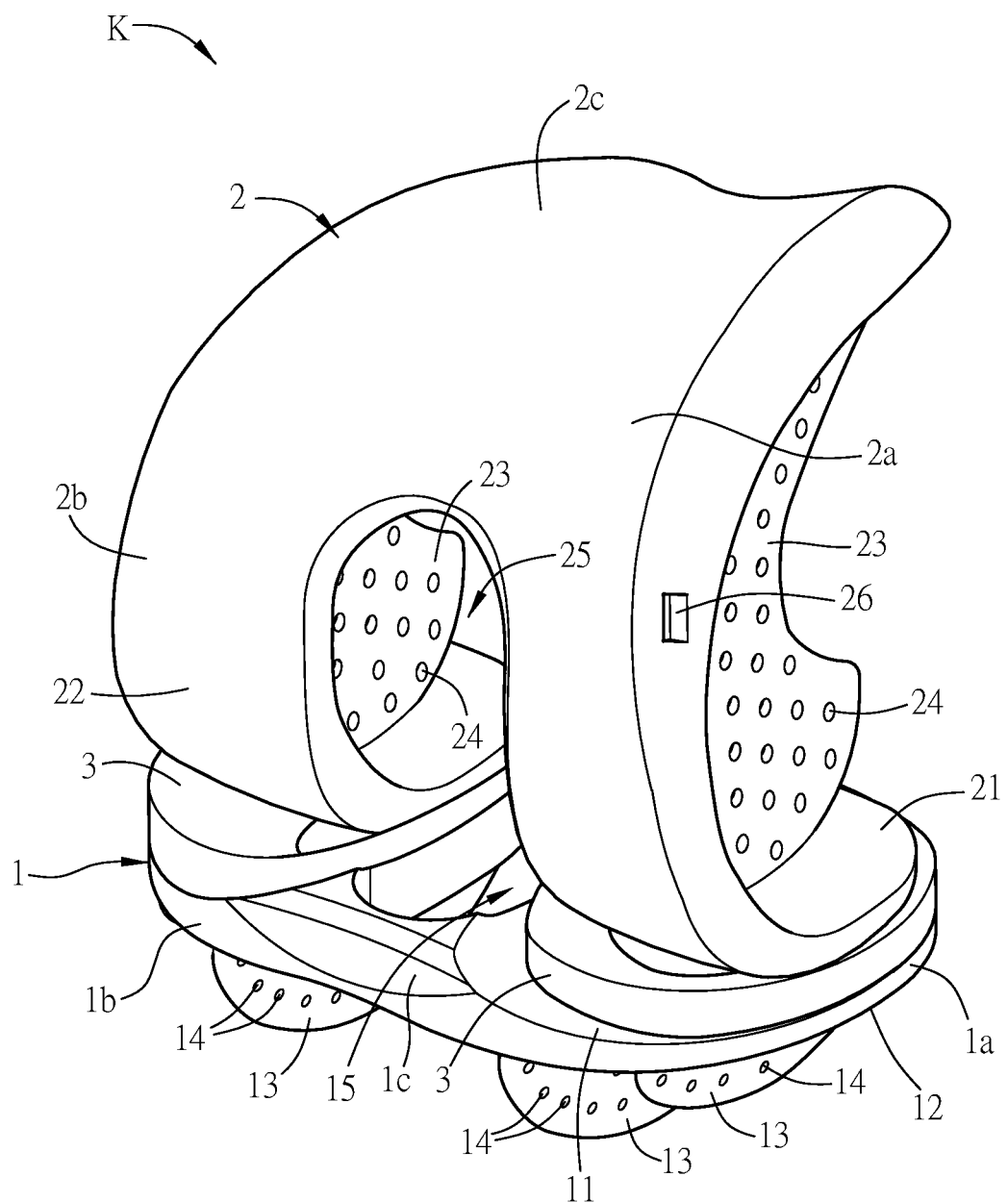
FIG. 1 is a schematic diagram showing the assembly of the knee joint prosthesis according to an embodiment.
Figure 4A:
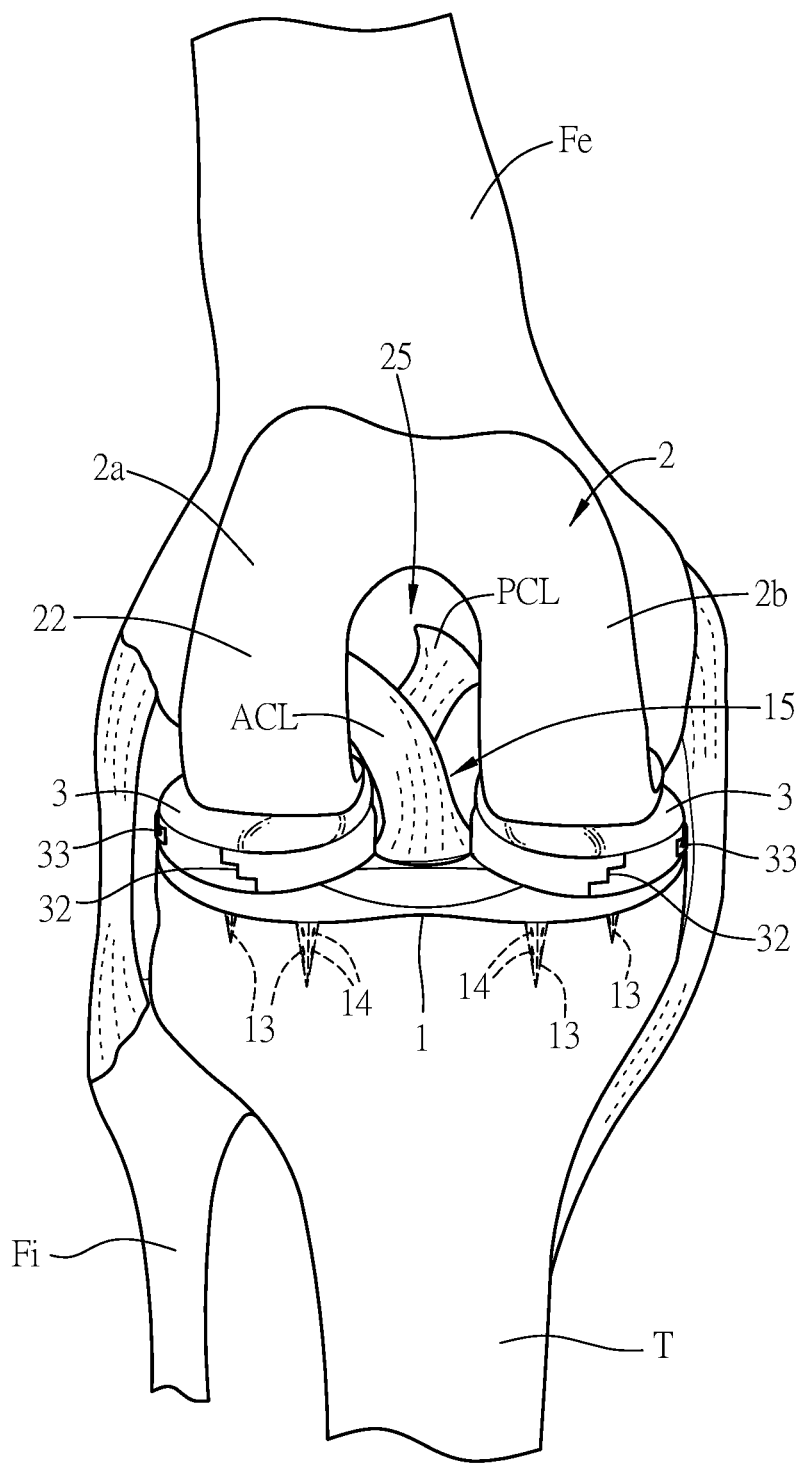
FIG. 4A is a schematic diagram showing the knee joint prosthesis in FIG. 1 is implanted into the patient's knee and observed in the anterior-posterior direction.
Figure 4B:
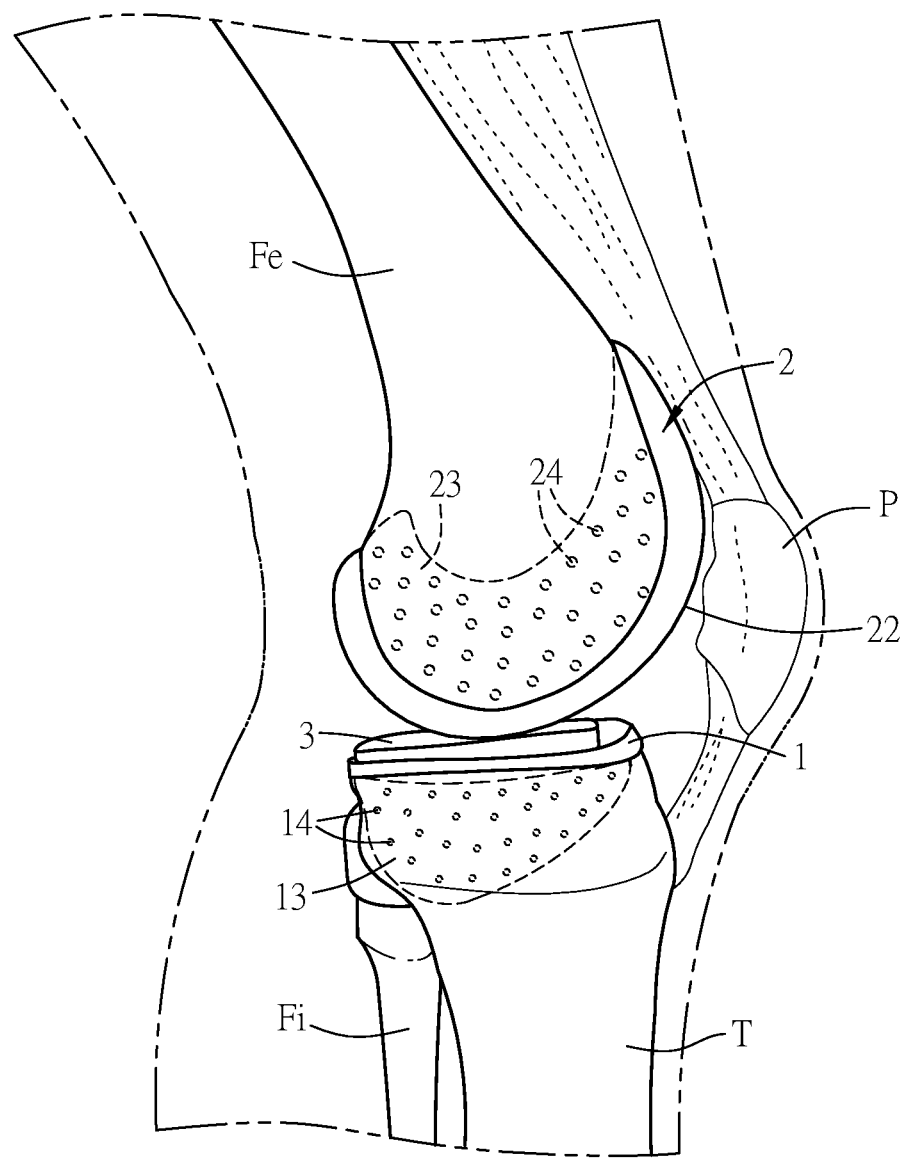
FIG. 4B is a schematic diagram showing the knee joint prosthesis in FIG. 1 is implanted into the patient's knee and observed in the medial-lateral direction.

First, referring to FIG. 1, FIG. 4A and FIG. 4B, FIG. 1 is a schematic diagram showing the assembly of the knee joint prosthesis according to an embodiment, FIG. 4A and FIG. 4B are schematic diagrams showing the knee joint prosthesis in FIG. 1 is implanted into the patient's knee. In FIG. 4A, the observed direction is the anterior-posterior direction of the patient's knee, and in FIG. 4B, the observed direction is the medial-lateral direction of the patient's knee. The relative positions of the femur Fe, the tibia T, the fibula Fi and the patella P shown in the figures are diagrammatic. The person skilled in the art should understand the relative positions and disposal relationship of the femur Fe, the tibia T, the fibula Fi and the patella P after implanting the knee joint prosthesis K in the embodiment according to the figures and the description. The knee joint prosthesis K includes a tibial component 1 and a femoral component 2. The tibial component 1 includes a top surface 11 and a bottom surface 12 opposite to the top surface 11. The tibial component 1 has at least one first protrusion 13 disposed on the bottom surface 12. In the embodiment, a plurality of the first protrusions 13 are disposed for example. Each of the first protrusions 13 has at least one first through hole 14. In the embodiment, a plurality of the first through holes 14 are disposed for example. The femoral component 2 is disposed corresponding to the tibial component 1, and the top surface 11 of the tibial component 1 carries the femoral component 2. In the embodiment, "carry" means two manners: a surface 22 the femoral component 2 facing the tibial component 1 directly abuts the top surface 11 of the tibial component 1; or alternatively, an additional component (descripted later) is utilized to buffer, so the femoral component 2 is supported on the top surface 11 of the tibial component 1 and the surface 22 of the femoral component 2 facing the tibial component 1 does not directly contact the top surface 11 of the tibial component 1 in an indirect carrying manner. In details, the femoral component 2 is slidably positioned at the tibial component 1. As shown in the figure, the top surface 11 of the tibial component 1 faces the surface of the femoral component 2 for engaging with the pad 3. After implanted, the bottom surface 12 of the tibial component 1 substantially contacts the surface of the tibia proximal end. The material of the tibial component 1 can be biocompatible metal material, for example but not limited to titanium, titanium alloy, Co—Cr—Mo alloy (cobalt-chromium-molybdenum alloy) or 316 stainless steel.

Figure 2:
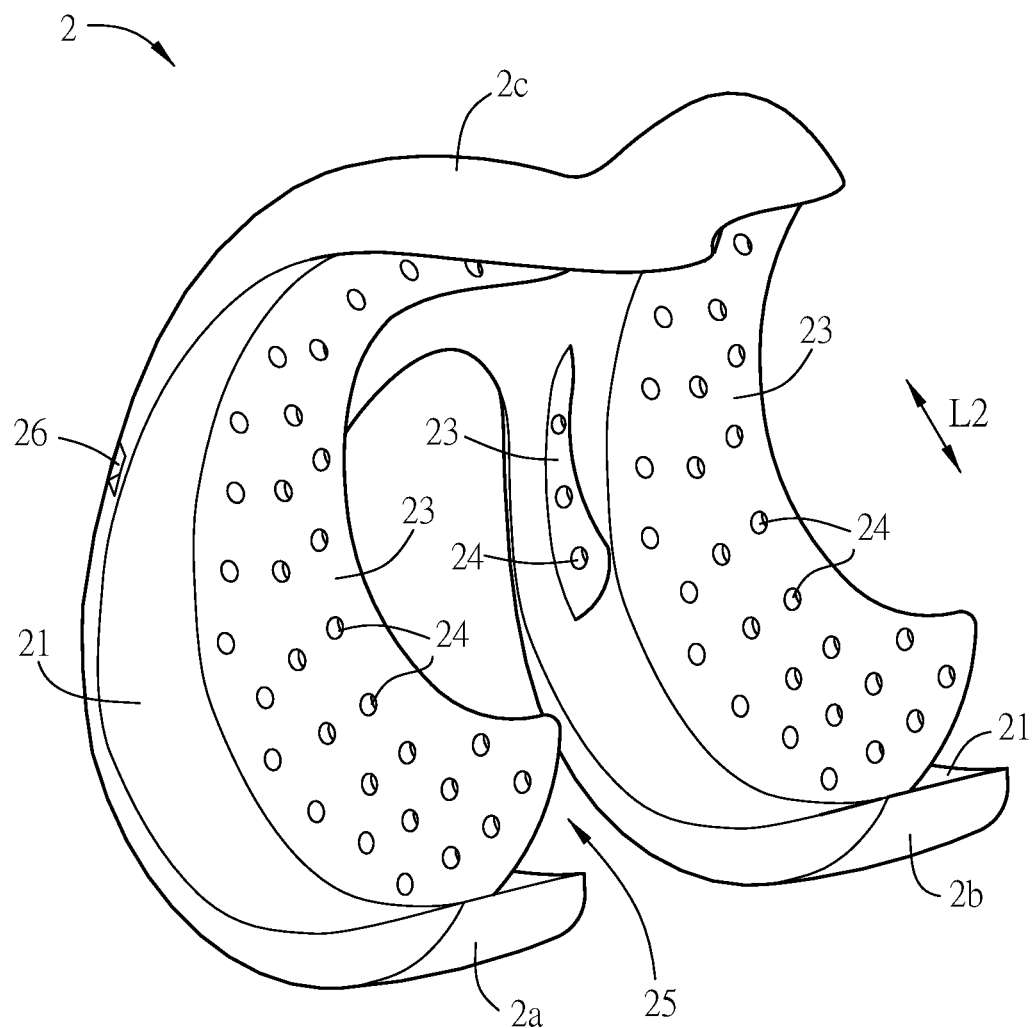
FIG. 2 is a schematic diagram showing the femoral component of the knee joint prosthesis in FIG. 1.
Figure 3:
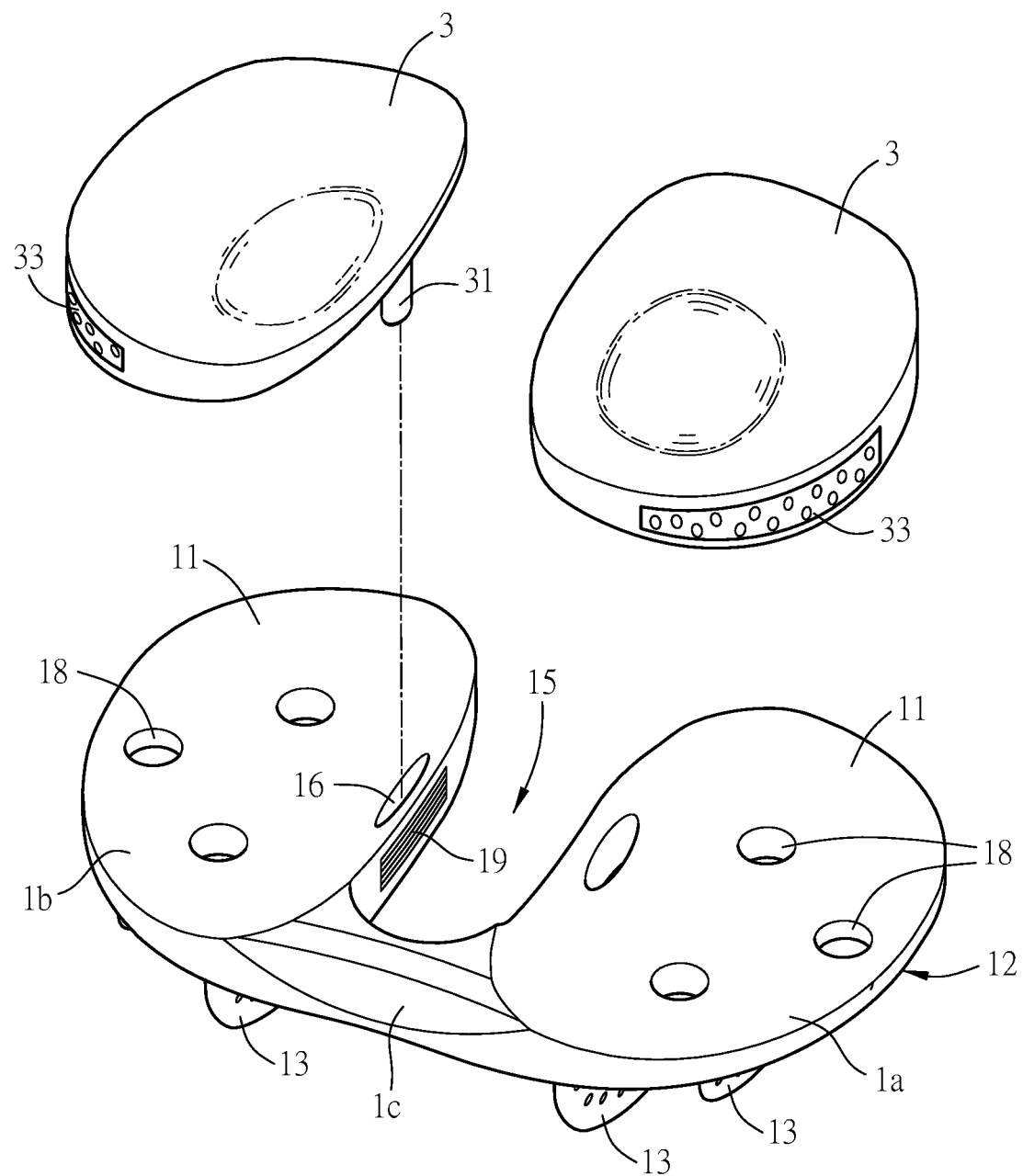
FIG. 3 is a schematic diagram showing the tibial component and the pad of the knee joint prosthesis in FIG. 1.

Referring to FIG. 1 to FIG. 3, FIG. 2 is a schematic diagram showing the femoral component of the knee joint prosthesis in FIG. 1, and FIG. 3 is a schematic diagram showing the tibial component and the pad of the knee joint prosthesis in FIG. 1. The femoral component 2 roughly looks like an arc and includes a second slot 25 which divides the femoral component 2 into a lateral condyle portion 2a and a medial condyle portion 2b connected by a connection portion 2c. Moreover, the connection portion 2c can also act as the sliding surface of the patella P as shown in FIG. 4B. FIG. 3 is a schematic diagram showing the tibial component and the pad of the knee joint prosthesis in FIG. 1. Besides, the tibial component 1 also includes a first slot 15 which passes through the top surface 11 and the bottom surface 12 and divides the tibial component 1 into a first portion (lateral side) 1a and a second portion (medial side) 1b. The first portion 1a and the second portion 1b are connected by the connection portion 1c. The lateral condyle portion 2a of the femoral component 2 is correspondingly and slidably disposed on the first portion (lateral side) 1a of the tibial component 1; similarly, the medial condyle portion 2b of the femoral component 2 is correspondingly and slidably disposed on the second portion (lateral side) 1b of the tibial component 1.

To easily hold the femoral component 2 for the surgeon in a surgical operation to aim and to press for implantation, at least one holding notch 26 is disposed at each of the two opposite sides of the femoral component 2 with respect to the second slot 25 for clamping and pressing. In other words, the second slot 25 is disposed between the two holding notches 26. The holding notch 26 may be a rectangle notch, a wedge notch or a ball notch, but it is not limited thereto. It is required to match the clamping apparatus for operation. The quantity of holding notch 26 is not limited, too.

Moreover, the depth of the first slot 15 in the sagittal axial is preferably 30% to 90% of the length of the tibial component 1 in the sagittal axial, more preferably 50% to 80%, so as to accommodate the anterior cruciate ligament ACL and the posterior cruciate ligament PCL by the first slot 15 (as shown in FIG. 4A. The projection length of the depth of the second slot 25 on the traverse plane of the patient's knee along the sagittal axial is preferable 30% to 90% of that of the femoral component 2 on the traverse plane of the patient's knee along the sagittal axial, more preferably 50% to 80%, so as to benefit the second slot 25 to accommodate the anterior cruciate ligament ACL and the posterior cruciate ligament PCL. The measurement of the depth and length mention above is based on that the tibial component 1 and the femoral component 2 are implanted into the patient's knee and buckling angle is zero (equivalently the patient stands or the lower limbs get straight). The person skilled in the art should understand that the ratio of the depth of the first slot 15 to the length of the tibial component 1 on the sagittal axial and the ratio of the depth of the second slot 25 to the projection length of the femoral component 2 on the traverse plane of the patient's knee along the sagittal axial are not necessarily equal. The first slot 15 and the second slot 25 are required to accommodate the anterior cruciate ligament ACL and the posterior cruciate ligament PCL, and they can be adjusted depending on actual situation.

Referring to FIG. 1, FIG. 4A and FIG. 4B, after the tibial component 1 is implanted into the tibial plateau of the patient, the first protrusions 13 are inserted into the tibial plateau. The tibial plateau means the portion of the tibia T which looks like a platform at the tibia proximal end. In the postoperative healing process, the bone trabeculae will grow to pass through the first through holes 14 on the first protrusions 13 so as to fix the tibial component 1 to the tibial plateau. Moreover, if it needs replacement in the future due to component wear, after implanting the new tibial component 1, the bone trabeculae will grow in the first through hole 14 to fix the replaced tibial component 1. Moreover, the more quantity of the first through holes 14 on the first protrusions 13, the better performance of fixing the tibial component 1 resulting from that the bone trabeculae grows to pass through the first through holes 14 to grasp the first protrusions 13. The thickness of the first protrusion 13 is preferably between 0.1 cm to 0.7 cm, more preferably between 0.3 cm and 0.4 cm. The thickness of the first protrusion 13 means the thickness of the connection portion of the first protrusion 13 connecting to the bottom surface 12. Moreover, in a preferable example, each of the first protrusions 13 has a plurality of the first through holes 14. The first through holes 14 on the first protrusion 13 are distributed from sparse to dense along the direction from close to the tibial component 1 to departing from the tibial component 1. The hole diameter of the first through hole 14 is preferably between 1 mm and 2 mm, and the interval between the first through holes 14 are preferably between 3 mm to 5 mm. Moreover, in one embodiment, the surface of each first protrusion 13 may be processed to form a rough surface by for example abrasive blasting or chemical etching. As a result, in the postoperative healing process, the bone trabeculae will grow on the surface of the first protrusion 13.

Referring to FIG. 8, to abate the risk of crash of the first protrusion 13 in implantation process, the first protrusion 13 may further have a first base 132 and a first cutting edge 131. The first base 132 may be rectangle (like (a) in FIG. 8B), square (like (b) in FIG. 8B), strip shape, trapezoid (like (c) and (d) in FIG. 8B), wedge, etc., but it is not limited thereto. It is required to have a wider contact base where the first cutting edge 131 can be stably disposed. The first cutting edge 131 extends opposite the tibial component 1 (namely, from the bottom surface 12 to the distal tibial). Meanwhile, the first cutting edge 131 gradually becomes thinner along the extending direction thereof.

The femoral component 2 has at least one second protrusion 23 disposed on the surface 21 against the tibial component 1. In the embodiment, a plurality of the second protrusions 23 are disposed for example. Each of the second protrusions 23 has at least one second through hole 24. In the embodiment, a plurality of the second through holes 24 are disposed for example. As shown in FIG. 2, the surface 21 of the femoral component 2 against the tibial component 1 is the inner surface of the femoral component 2 looking like an arc structure, and substantially contacts the femur distal end after implanted. The material of the femoral component 2 can similarly be biocompatible metal material, for example but not limited to titanium, titanium alloy, Co—Cr—Mo alloy or 316 stainless steel. Similarly to the first protrusion 13, to abate the risk of crash of the second protrusion 23 in implantation process, the second protrusion 23 may have a the second base and a second cutting edge (not shown in the figure). The configuration of the second base is the same or similar with the first base 132. It is required to have a wider contact base where the second cutting edge can be stably disposed. The second cutting edge extends against the arc inner surface 21 of the tibial component 1 (namely, from the surface 21 to proximal femoral). Meanwhile, the second cutting edge gradually becomes thinner along the extending direction thereof.

Similar to the tibial component 1, as to the femoral component 2 implanted into the femoral condyles of the femur Fe, the second protrusion 23 will be inserted into the corresponding femoral condyles. In the postoperative healing process, the bone trabeculae will grow to pass through the second through hole 24 on the second protrusion 23 so as to fix the femoral component 2 to the femoral condyles. Moreover, if it needs replacement in the future due to component wear, after implanting the new femoral component 2, the bone trabeculae will grow in the second through hole 24 to fix the replaced femoral component 2. The preferable thickness of the second protrusion 23 is between 0.1 cm to 0.7 cm, more preferably between 0.3 cm and 0.4 cm. Here, the thickness of the second protrusion 23 means the thickness of the second protrusion 23 connecting to the surface 21. Moreover, in a preferable example, each of the second protrusions 23 has a plurality of the second through holes 24. The second through holes 24 on the second protrusion 23 are distributed from sparse to dense along the direction from close to the femoral component 2 to departing from the femoral component 2. The hole diameter of the second through hole 24 is preferably between 1 mm to 2 mm, and the interval between the second through holes 24 is preferably between 3 mm to 5 mm. Moreover, in one embodiment, the surface of each second protrusion 23 may be processed to form a rough surface by for example abrasive blasting or chemical etching. As a result, in the postoperative healing process, the bone trabeculae will grow on the surface of the second protrusion 23.

Besides, although the first protrusion 13 and the second protrusion 23 in the embodiment are integrated as a whole one element on the bottom surface 12 of the tibial component 1 and the arc inner surface 21 of the femoral component 2 against the tibial component 1 for example, they are not limited thereto. Namely, in other embodiments, the first protrusion 13 and the second protrusion 23 can be detachable, during usage, it is assembled with the bottom surface 12 of the tibial component 1 and the arc inner surface 21 of the femoral component 2 against the tibial component 1.

Referring to FIG. 4A and FIG. 4B, after implanting the tibial component 1 into the tibial plateau of the patient, the anterior cruciate ligament ACL and the posterior cruciate ligament PCL of the patient's knee are accommodated in the first slot 15. Similarly, after implanting the femoral component 2 into the femur distal end of the patient, the anterior cruciate ligament ACL and the posterior cruciate ligament PCL of the patient's knee are accommodated in the second slot 25. Thus, after the orthopedic surgeon performs keen joint replacement to implant the knee joint prosthesis K into the patient's knee, one can adopt cruciate ligament-retaining namely retain the anterior cruciate ligament ACL and the posterior cruciate ligament PCL of the patient instead of resection during implanting to keep the stability of the patient's postoperative joint and reduce the wear of the new joint. Moreover, the postoperative knee can keep considerable exercise freedom (for example buckling, stretching, outward rotation, inward rotation, eversion and inversion, etc.).

Figure 8A:
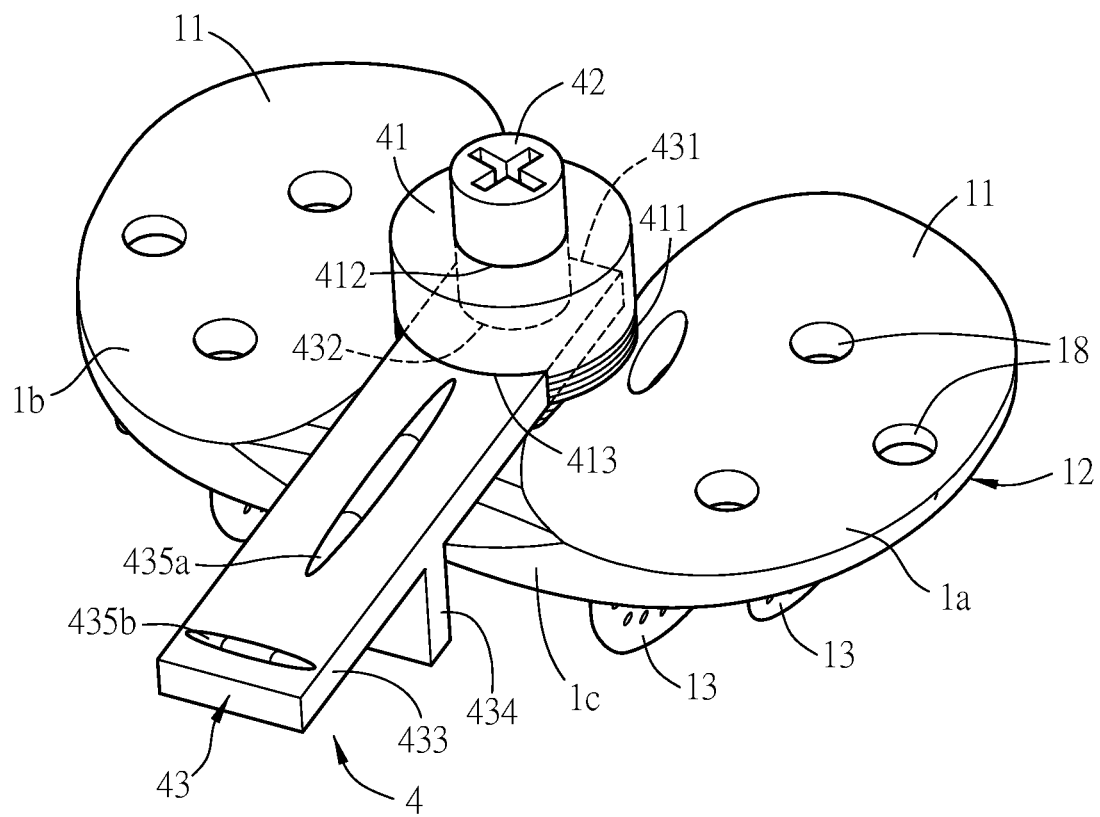
FIG. 8A is a schematic diagram showing the tibial component of the knee joint prosthesis in FIG. 1 and auxiliary implantation device.
Figure 8B:
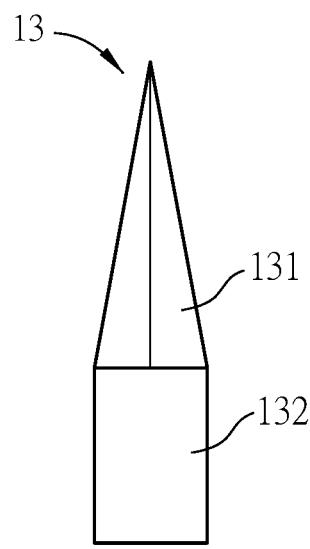
FIG. 8B to FIG. 8D are schematic diagrams showing the first protrusion in the tibial component of the knee joint prosthesis in FIG. 2.
Figure 8B:
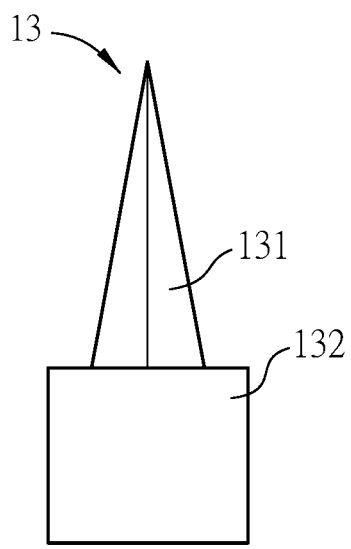
Figure 8B:
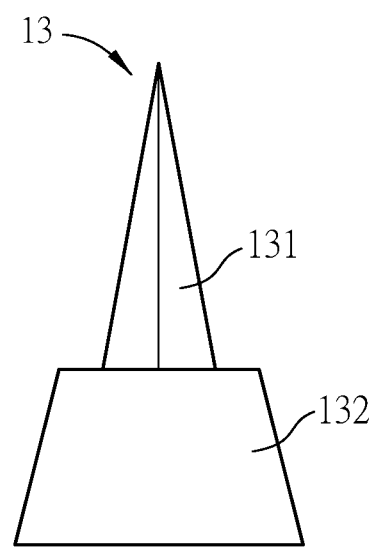
Figure 8B:
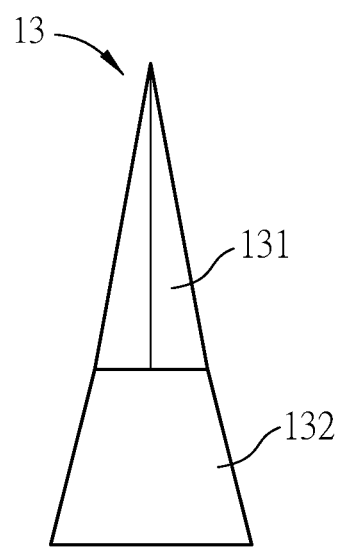

For easily implanting the tibial component 1, in the embodiment, the first protrusion 13 extends along a direction against the tibial component 1 (namely extends from the bottom surface 12 toward the tibia distal end). Concurrently, the first protrusion 13 gradually becomes thinner along the extending direction of the first protrusion 13 and it is like a fin or a blade. The method of implanting the tibial component 1 includes but is not limited to nailing (directly making the tibial component 1 abut the tibia proximal end and applying a force substantially parallel to the tibia the longitudinal direction, and thwacking the tibial component 1 into the tibial plateau), slide-in (sliding along the direction of anterior-to-posterior of the knee and inserting obliquely downwardly), adhesion (applying bone cement or biological glue to the bottom surface 12 so that the tibial component 1 is adhered to the tibial plateau), or any combination of the previous methods. To smooth the implantation of the tibial component 1, an additional auxiliary implantation device can be used. Referring to FIG. 8A, auxiliary implantation device 4 comprises a position block 41, a fixing screw 42, and a wrench 43. The position block 41 is approximately a cylinder, a plurality of position grooves 411 (may be parallel grooves or screw thread) are disposed on each of two opposite outer side surfaces thereof or disposed around the outer side surface thereof, and it has a fixing screw hole 412 where fixing screw 42 is screwed. The fixing screw hole 412 extends inwardly along its major axis from one end of the position block 41. The first portion 1a, the connection portion 1c and the second portion 1b of the tibial component 1 comprise at least one sidewall which surrounds the first slot 15, and the engagement grooves (maybe parallel grooves or screw thread) 19 (as shown in FIG. 3) are disposed on the sidewall. By using the position grooves 411 on the outer side surface of the position block 41 and the engagement grooves 19 on the sidewall, the position block 41 can be screwed or embedded with the tibial component 1. One end of the wrench 43 is a lock end 431, the other end opposite to the lock end 431 is a handle end 433. The lock end 431 further has a lock hole 432. In other embodiments, the lock end 431 may not have the lock hole 432. The wrench 43 further has an abutting wall 434 disposed between the lock end 431 and the handle end 433, preferably near the lock end 431. The position block 41 further comprises an opening 413 where the lock end 431 of the wrench 43 is inserted. The opening 413 extends from the outer side surface of the position block 41 inwardly along the direction approximately perpendicular to the major axis of the position block 41.

When the lock end 431 of the wrench 43 is inserted into the opening 413 of the position block 41, the lock hole 432 is aligned to the fixing screw hole 412 and then the fixing screw 42 can be inserted into the fixing screw hole 412 and the lock hole 432 to secure the position block 41 to the wrench 43. In other embodiments, because the lock end 431 does not have the lock hole 432, when the lock end 431 of the wrench 43 is inserted into the opening 413 of the position block 41, the fixing screw 42 can be inserted into the fixing screw hole 412 to secure the position block 41 to the wrench 43. Therefore, it is possible to omit to align the lock hole 432 to the fixing screw hole 412. Meanwhile, the abutting wall 434 abuts the connection portion 1c of the tibial component 1. Thus, it seems that the abutting wall 434 of the wrench 43 and the position block 41 clamp the connection portion 1c. Therefore, in implanting the tibial component 1, by using the rear portion of the first protrusion 13 of the tibial component 1 to abut the patient's tibial plateau, the surgeon can take the place of the patient's tibial plateau abutted by the first protrusion 13 as the fulcrum and hold the handle end 433 of the wrench 43, and then slides the first protrusion 13 of the tibial component 1 into the patient's tibial plateau. Further, gradienters 435, 436 can be disposed on the wrench 43 so the surgeon can observe that the first portion 1a and the second portion 1b of the tibial component 1 both are horizontal to the same level after implanting the tibial component 1.

Figure 4C:
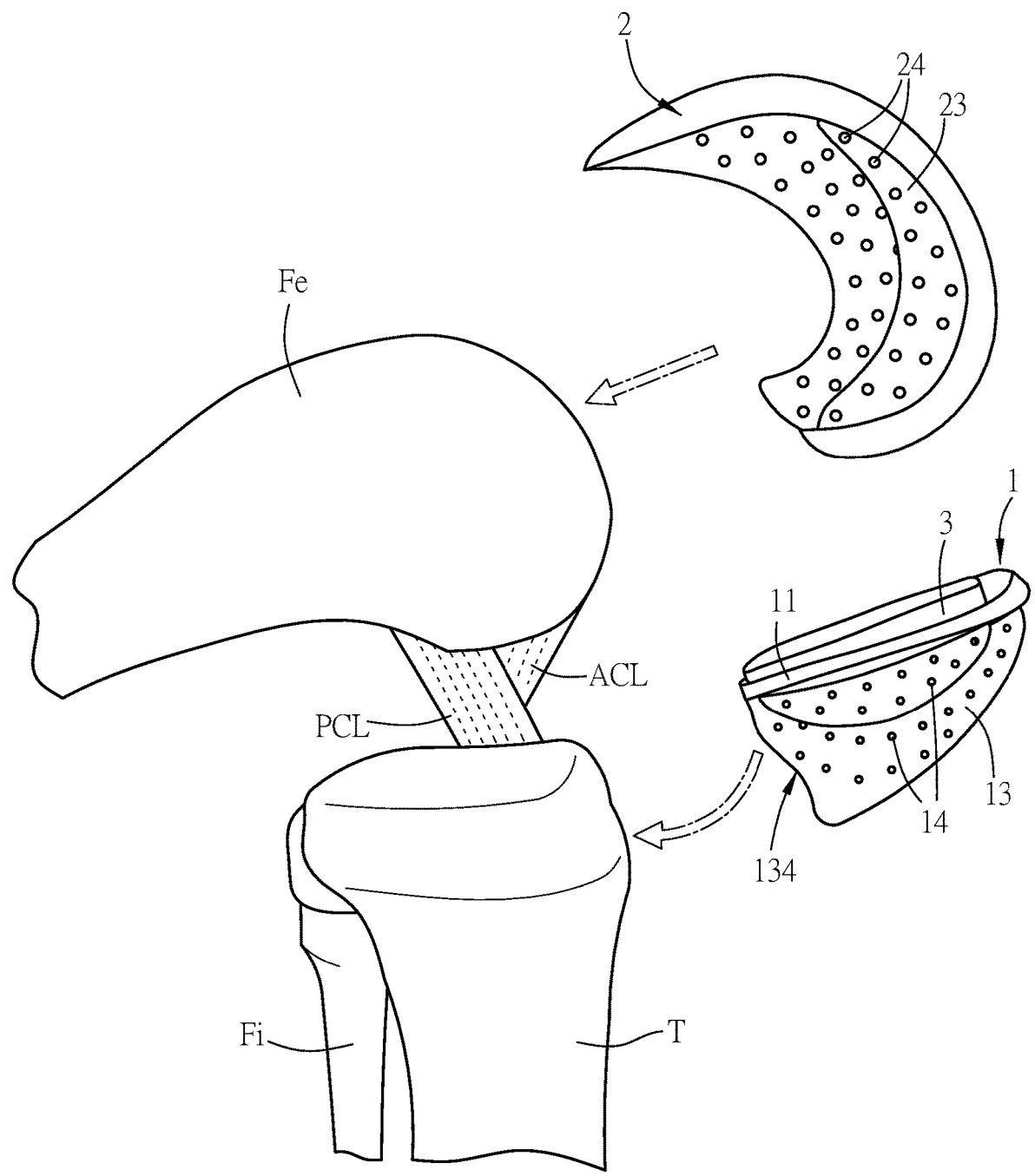
FIG. 4C is a schematic diagram showing the direction for implanting the tibial component and the femoral component of the knee joint prosthesis in FIG. 1 into the patient's knee.
Figure 8C:
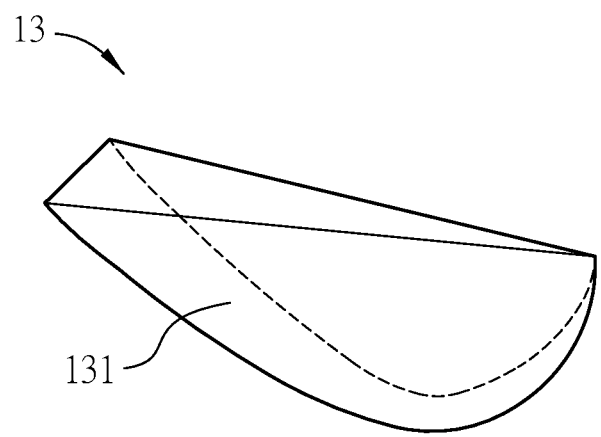
Figure 8D:
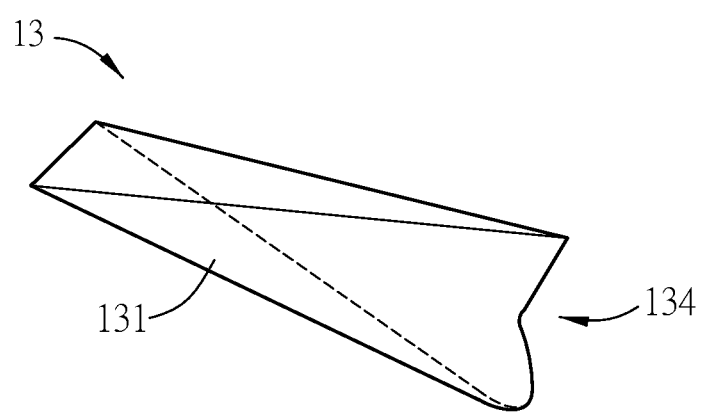

Referring to FIG. 8C, the first protrusion 13 may be thinner and extend longer at its rear portion so the rear portion is sharper and the front portion is blunter (like cleaver). In the implanting process, the rear portion of the first protrusion 13 of the tibial component 1 contact and abut the patient's tibial plateau first. As a result, in implanting the tibial component 1 in the patient's tibia condyle by sliding, the sharper rear portion of the first protrusion 13 firstly breaks the bone tissue of the patient's tibia condyle, and then the middle segment and the front portion of the first protrusion 13 can accordingly smoothly cut into the bone tissue of the patient's tibia condyle to complete the implantation of the tibial component 1. Moreover, because after implantation, the posterior of the tibial component 1 carries heavier weight than the anterior does. The extension of the rear portion of the first protrusion 13 is longer than the extension of the front portion of the first protrusion 13 so as to stably support the tibial component 1. It is noted that although the first through holes are omitted in FIG. 8C, actually the first protrusion 13 comprises a plurality of the first through holes 14. Referring to FIG. 8D and FIG. 4C, a receded incision 134 may be disposed on the rear portion of the first protrusion 13 to preferably conform the tibia T. Moreover, when implanting the tibial component 1 in the patient's tibia condyle by sliding, the receded incision 134 on the first protrusion 13 abutting the patient's tibial plateau can act as the point applied with force, and it is also a guide for the surgeon to press downwardly. The receded incision 134 let the first protrusion 13 completely covered by bone tissue in the implantation process and reserve some gaps, too. Therefore, it prevents the first protrusion 13 from being stuck when cutting into the tibial plateau. It is easier for the first protrusion 13 to slide into the patient's tibial plateau. It is noted that although the first through holes 14 are omitted in FIG. 8D, actually the first protrusion 13 comprises a plurality of the first through holes 14. Moreover, the extension of the first protrusion 13 may be alternatively various in length along it major axis, such as a mountain having summits and valleys arranged alternatively along its ridgeline, so the first protrusions 13 cut into the tibial plateau in various depth.

Similarly, for easily implanting the femoral component 2, in the embodiment, the second protrusion 23 extends a direction against the femoral component 2 (namely extends from the surface 21 toward the proximal end direction of the femur). Concurrently, the second protrusion 23 gradually becomes thinner along the extending direction of the second protrusion 23 and it is like a fin or a blade. The method of implanting the femoral component 2 preferably is nailing or pushing (directly making the femoral component 2 abut the femur distal end and applying a force substantially parallel to the femur the longitudinal direction, and thwacking the femoral component 2 into the femoral condyles). Moreover, the extension of the second protrusions 23 may be alternatively various in length along it major axis, such as a mountain having summits and valleys arranged alternatively along its ridgeline, so the second protrusions 23 are thwacked into the femoral condyles in various depth.

Figure 8E:
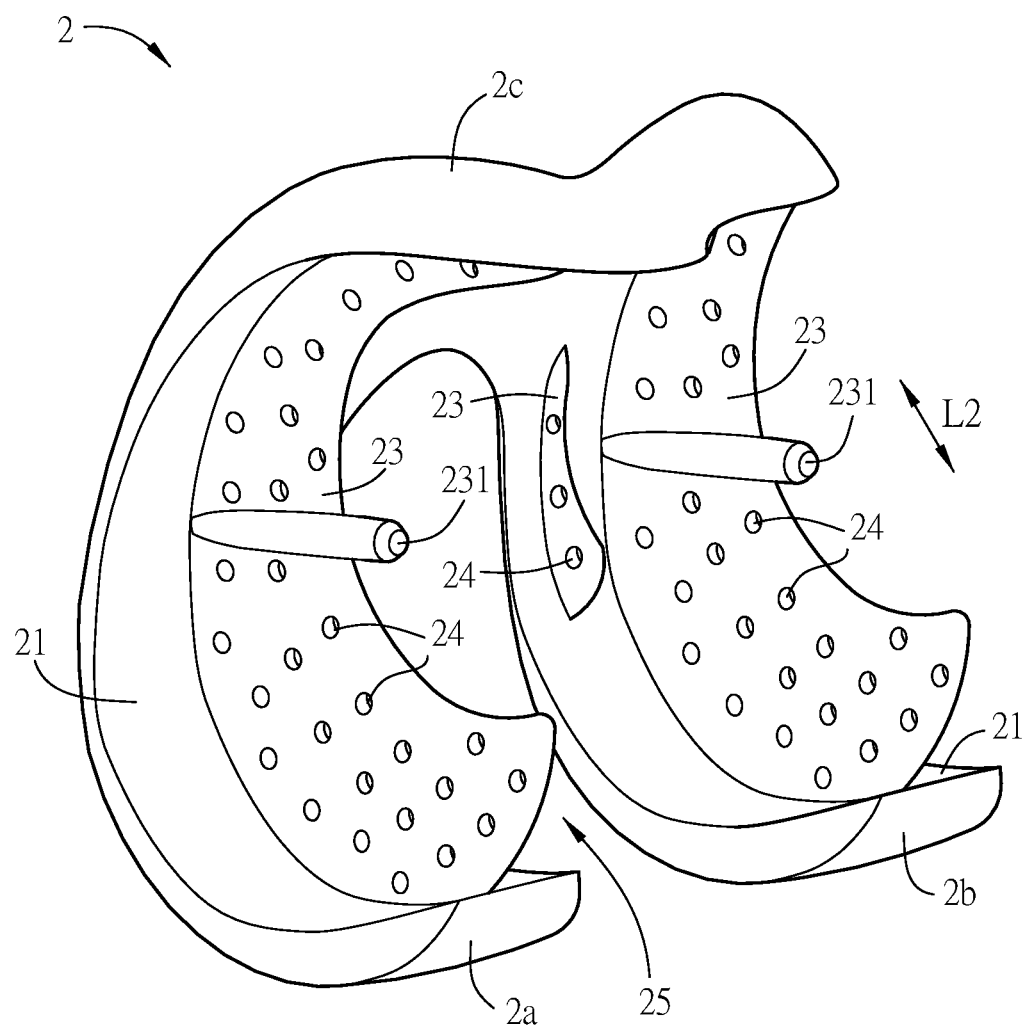
FIG. 8E is a schematic diagram showing another femoral component of the knee joint prosthesis according to another embodiment.
Figure 9A:
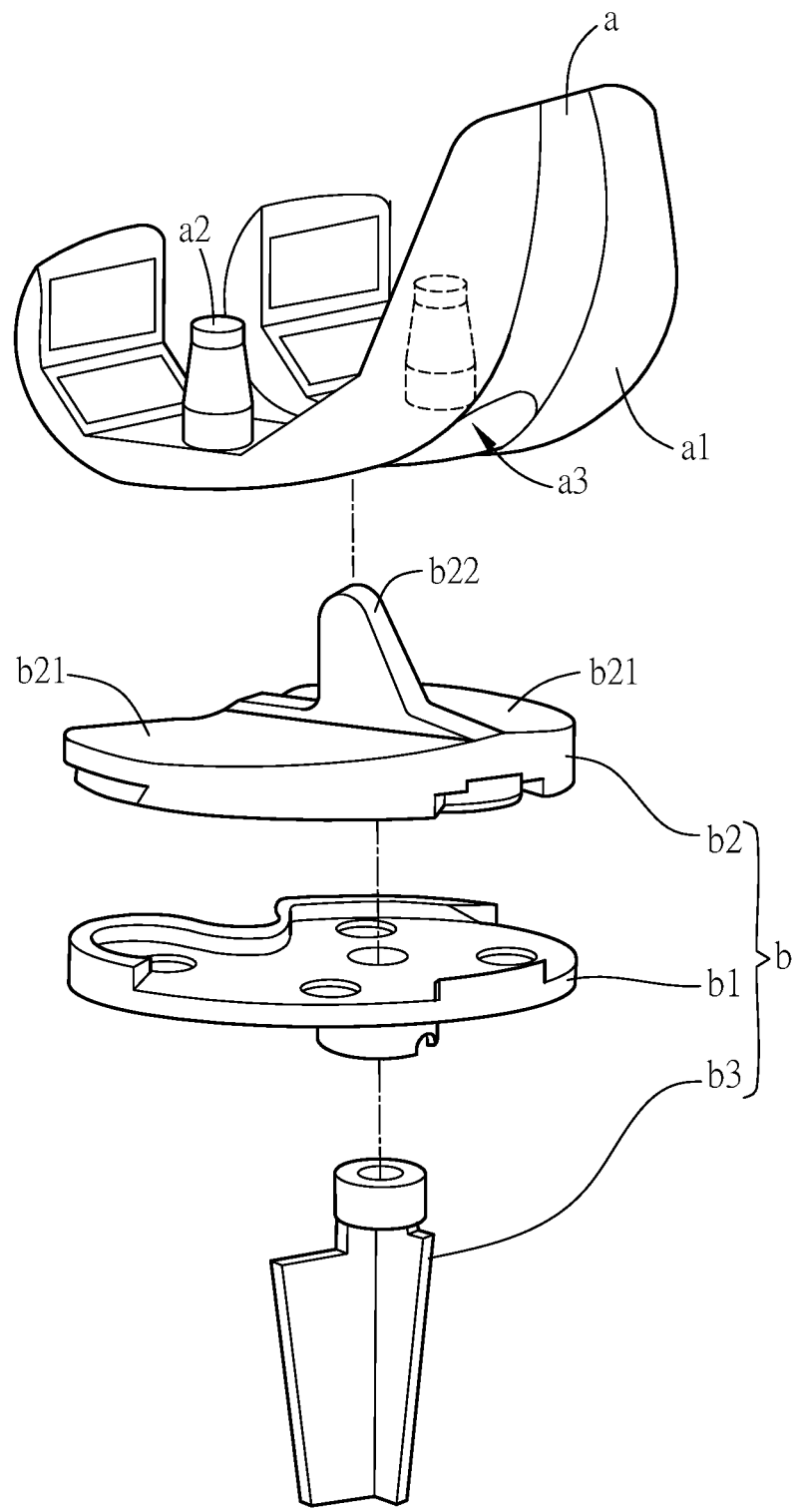
FIG. 9A to FIG. 9B are schematic diagrams showing the conventional knee joint prosthesis.
Figure 9B:
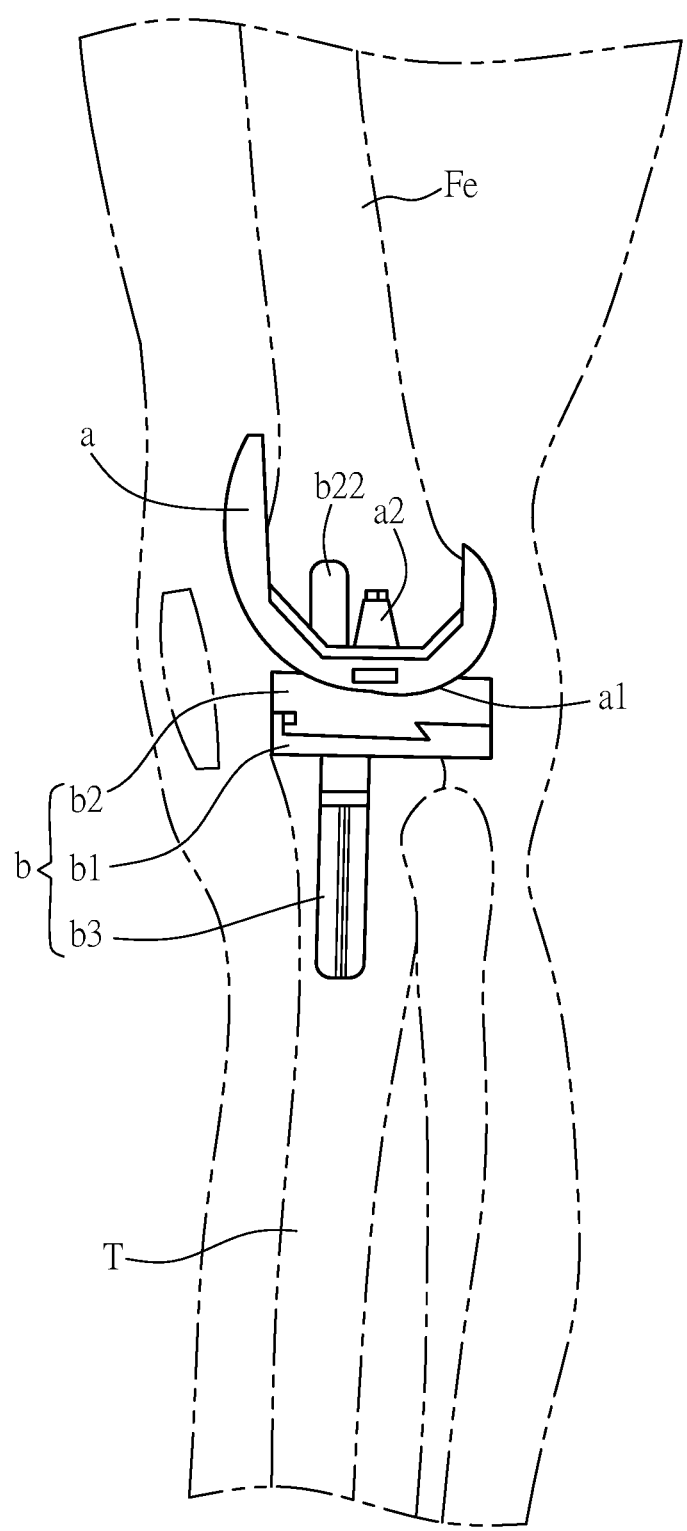

Moreover, referring to FIG. 8E, to prevent the implanted femoral component 2 from moving on sagittal plane, the second protrusion 23 may further comprise a position pillar 231 disposed on the middle segment, or on a location near the middle segment, of the second protrusion 23 which is like fin or knife. Thus, before implanting, position holes should be drilled in the corresponding femoral condyle. As a result, after implanting the femoral component 2 in the corresponding femoral condyle, the second protrusion 23 is inserted into the corresponding femoral condyle as mentioned previously, and the position pillar 231 is inserted into the position hole drilled in the femoral condyle. Thus, the femoral component 2 can be stably disposed, and it slide or rotate over the sagittal plane as little as possible. In addition to nailing or pushing mentioned previously, the femoral component 2 can be implanted into the patient's femoral condyle by slide-in (sliding along the direction of anterior-to-posterior of the knee and inserting obliquely upwardly), adhesion (applying bone cement or biological glue to the surface 21 against the tibial component 1 so that the femoral component 2 is adhered to the femoral condyles) or any combination of the previous methods. However, if implanting by sliding, preferably the position pillar 231 is omitted on the second protrusion 23.

Referring to FIG. 4C, it is a schematic diagram showing the direction for implanting the tibial component and the femoral component of the knee joint prosthesis in FIG. 1 into the patient's knee. When the orthopedic surgeons performs keen joint replacement, preferably, the outer cartilage of condyle of femoral Fe is processed first to lighten the damage to the patient's bone. For easily implanting the tibial component 1 or the femoral component 2 by slide-in, the extending direction of the first protrusion 13 or the second protrusion 23 is substantially parallel to the sagittal plane of the patient's knee. However, it is not limited thereto.

Figure 5A:
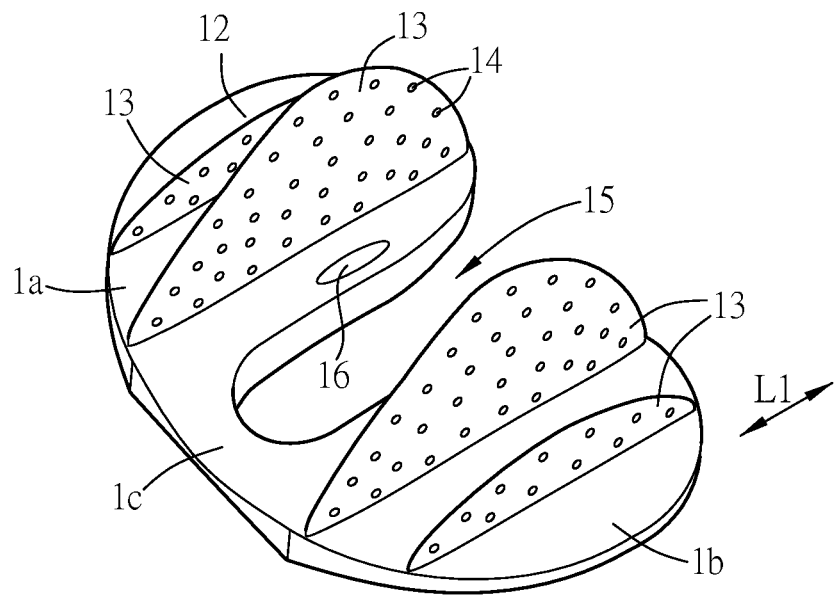
FIG. 5A to FIG. 5G are schematic diagrams showing the tibial component of the knee joint prosthesis in FIG. 1.
Figure 5B:
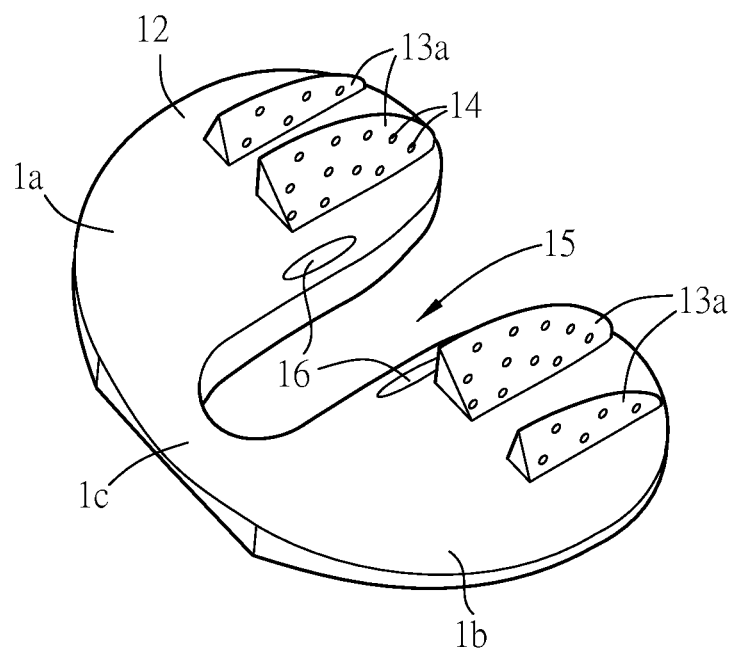
Figure 5C:
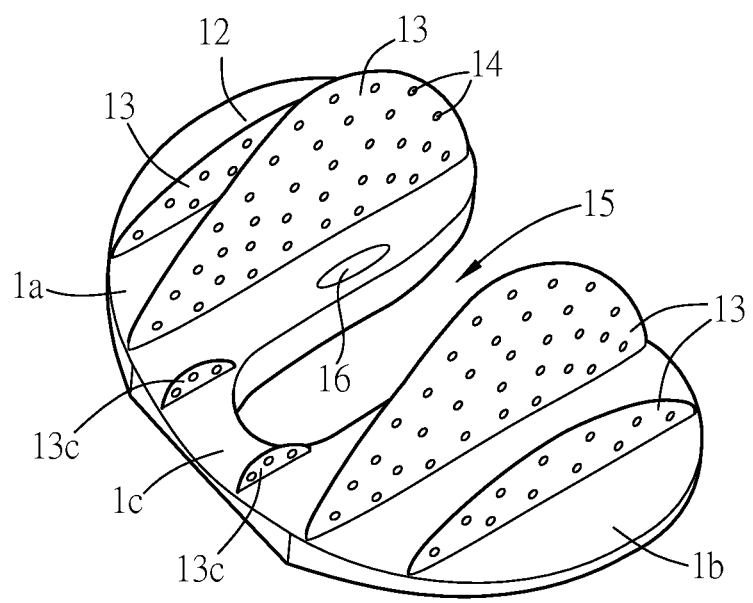

Referring to FIG. 5A to FIG. 5C, they are schematic diagrams showing the tibial component of the knee joint prosthesis in FIG. 1. Similarly, for easily implanting the tibial component 1 by slide-in, each of the first protrusions 13 of the tibial component 1 has a first longitudinal direction L1, which is parallel to its major axis, and each of the first longitudinal directions L1 is substantially parallel to each other. Besides, the fin structure or the blade structure of each of the first protrusions 13 in FIG. 5A extends from the front to the rear of tibial component 1 and looks like a complete arc structure. As shown in FIG. 5B, the fin structure or the blade structure of each of the first protrusions 13 extends only from the center to the rear and looks like a halt arc structure. Referring to FIG. 5C, for increasing the structure strength of the connection portion 1c and reducing the break of the connection portion 1c caused by stress due to low structure strength when implanted, at least one additional first protrusion 13c can be disposed on the bottom surface 12 of the connection portion 1c. Additional two are disposed in the figure for example.

Figure 5D:
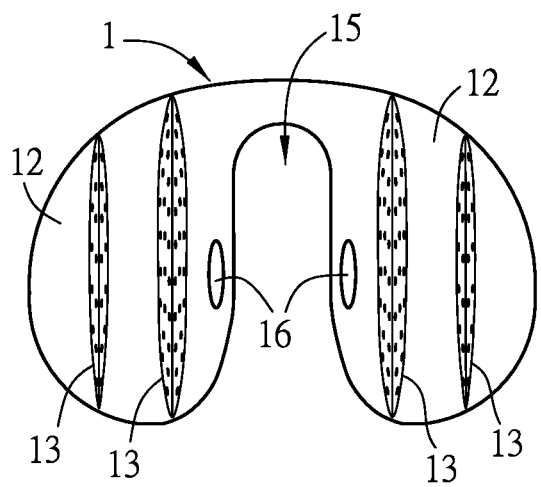
Figure 5E:
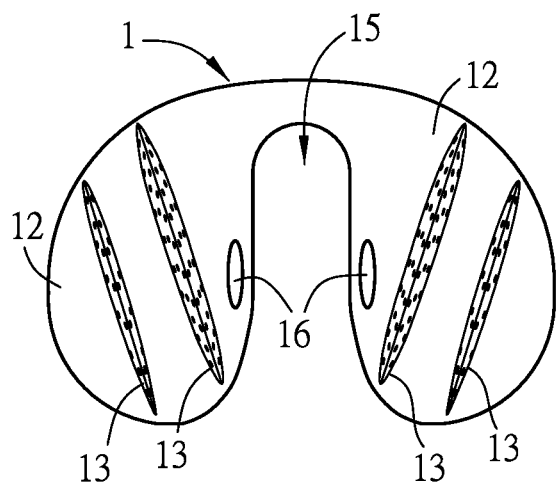
Figure 5F:
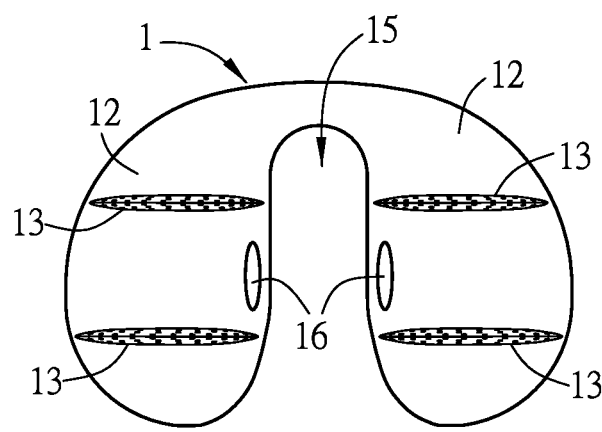
Figure 5G:
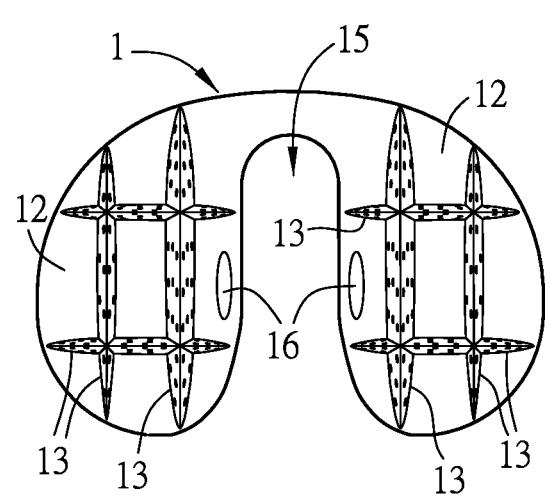

Besides, referring to FIG. 5D to FIG. 5G, they are schematic diagrams showing other examples of the tibial component 1 of the knee joint prosthesis in FIG. 1. When implanting by the method other than slide-in, the longitudinal direction of the first protrusion 13 can also be the direction along the coronal plane of the knee or other directions. Namely, as shown in FIG. 5D, the first protrusion 13 is disposed along the front-rear direction of the tibial component 1 and substantially parallel to the sagittal plane of the patient's knee, but alternatively as shown in FIG. 5E, the first protrusion 13 is roughly disposed along the front-rear direction of the tibial component 1 but not substantially parallel to the sagittal plane of the patient's knee. Or alternatively as shown in FIG. 5F, the first protrusion 13 is disposed along the medial-lateral direction of the tibial component 1 and substantially parallel to the coronal plane direction of the knee. Moreover, as shown in FIG. 5G, combining the above directions, the first protrusions 13 interlace on the bottom surface 12 of the tibial component 1.

Similar to the previous design of the first protrusion 13 in a preferable example for easily implanting by slide-in as shown in FIG. 2, each of the second protrusions 23 of the femoral component 2 has a second longitudinal direction L2, which is parallel to its major axis, and each of the second longitudinal directions L2 is substantially parallel to each other. However, they are not limited thereto. Namely, each of the second protrusion 23 can extend from the front to the rear of the femoral component 2 and look like a complete arc structure, or alternatively extend only from the center to the rear of the femoral component 2 and look like a half arc structure. Alternatively, the second protrusion 23 can be disposed along the sagittal plane, the coronal plane direction or other direction or combination of the previous directions of the knee.

Besides, in the embodiment, the knee joint prosthesis K further includes at least one pad 3. Referring to FIG. 1 and FIG. 3, the knee joint prosthesis K includes two pads 3 for example. The pads 3 are located between the tibial component 1 and the femoral component 2, and can be respectively engaged with the top surface 11 of first portion 1a and the top surface 11 of the second portion 1b. The top surface 11 of the first portion 1a or the top surface of the second portion 1b looks like a shallow-dish concave, and the surfaces of the two pads 3 which contact them are respectively designed with a convex corresponding to the shallow-dish concave. The pad 3 can have a circular pit. The surface facing the femoral component 2 can be designed to carry the lateral condyle portion 2a or the medial condyle portion 2b of the femoral component 2 and have an arc concave surface on which they can slide. Thus, the pads 3 act as the knee meniscus. In one embodiment, if the surface of the pad 3 facing the femoral component 2 is a curved concave, the thickness at the curved concave/the thickness at the periphery of the pad 3 may be 2 mm/6 mm, 3 mm/8 mm, 4 mm/10 mm, or 5 mm/12 mm. After implanted into the patient's knee, the femoral component 2 abuts the pad 3 and the femoral component 2 can slide or rotate with respect to the tibial component 1. Referring to FIG. 3, although the pad 3 in the embodiment for example but not limited to has a slidable curved concave and looks like a disk. The preference is that the pad 3 has a concave surface to carry the lateral condyle portion 2a or the medial condyle portion 2b of the femoral component 2 on which they can slide. Namely, the pad 3 having circular pit is also preferable. In the embodiment, the material of the pad 3 can be biocompatible plastic including but not limited to medical grade PVC, Polyethylene, PEEK, Polycarbonate, PEI resin (Ultem®, Polyetherimide resin), Polysulfone, Polypropylene or Polyurethane. Further, the pad 3 has a first engagement portion 31, the first engagement portion 31 fits the second engagement portion 16 of the tibial component 1, and the second engagement portion 16 of the tibial component 1 is adjacent to the first slot 15. As shown in FIG. 3, the second engagement portions 16 on the tibial component 1 in the embodiment are disposed on the first portion 1a and the second portion 1b close to the first slot 15. In a preferable example, when the pad 3 is disposed on the tibial component 1, they are connected to each other only by the first engagement portion 31 of the pad 3 and the second engagement portion 16 of the tibial component 1 at medial side. Moreover, the first engagement portion 31 of the pad 3 is a rod conformation and the second engagement portion 16 of the tibial component 1 is a circular through hole, so that the first engagement portion 31 of the pad 3 and the second engagement portion 16 of the tibial component 1 constitutes a pivot structure. The lateral of the pad 3 and the tibial component 1 are not fixed so the femoral component 2 of the implanted knee joint prosthesis K can still rotate in outward rotation and inward rotation with respect to the tibial component 1 to keep freedom of outward rotation and inward rotation of the patient's postoperative knee. However, the conformations of the first engagement portion 31 of the pad 3 and the second engagement portion 16 of the tibial component 1 are not limited. The first engagement portion 31 of the pad 3 can be the rod conformation mentioned above, or the first engagement portion 31a can be a bolt conformation in FIG. 6B or the bump in FIG. 6C for example but not limited to hemispherical bump or half-moon bump. In a preferable example in the embodiment, the fit between the first engagement portion 31 of the pad 3 and the second engagement portion 16 of the tibial component 1 is concave-convex. That which one is concave or which one is convex is not limited.

As shown in FIG. 3, the tibial component 1 further has at least one through hole 18 on the first portion (lateral) 1a and the second portion (medial) 1b. In the embodiment, there are a plurality of the through holes for example, but the quantity is not limited. The through hole 18 passes through the top surface 11 and the bottom surface 12 and preferably keeps away the location where the first protrusion 13 is disposed. Such design lets the tibial component 1 be lightweight and exhausts particles caused by the friction between the pad 3 and the tibial component 1. The diameter of the through hole 18 is preferably smaller than or equal to the distance between the two adjacent the first protrusions 13.

Figure 6A:
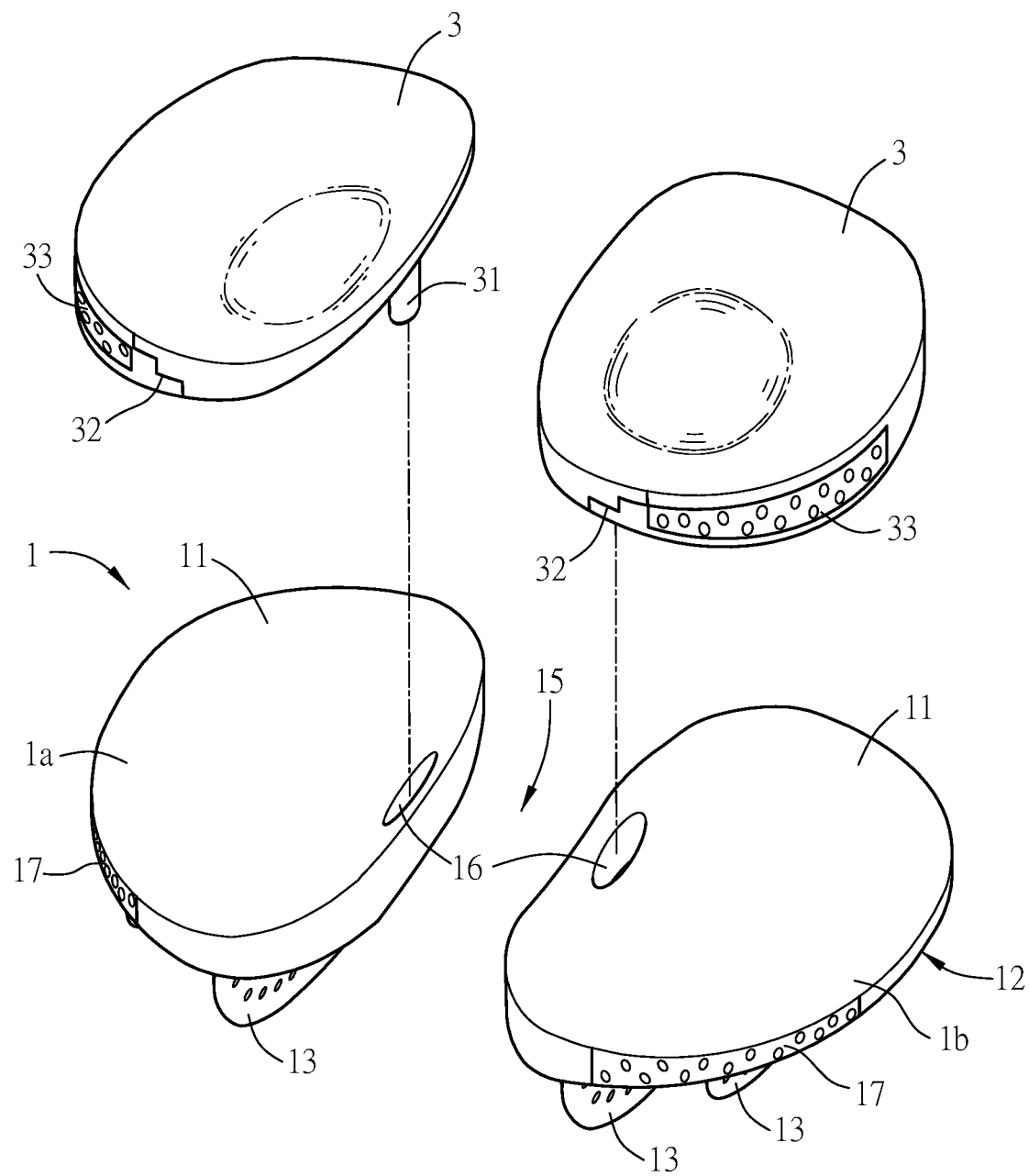
FIG. 6A to FIG. 6C are schematic diagrams showing the tibial component and the pad of the knee joint prosthesis in FIG. 1.

Moreover, a first side wall 33 may be disposed on the outer sidewall of the pad 3. The first side wall 33 has at least one first aperture. In the embodiment, there are for example but not limited to a plurality of the first apertures. In the postoperative healing process, the first apertures are tightly clutched by the tissue at the patient's implanted portion so the pad 3 and the patient's knee can act together and the postoperative stability becomes better. The dimension of the first aperture is the same or similar with the first through hole or the second through hole on the first protrusion 13 or the second protrusion 23. The height of the first side wall 33 is preferably equal to ⅔ of the thickness of the pad 3, but it is not limited thereto. The material of the first side wall 33 is biocompatible metal material including for example but not limited to titanium, titanium alloy, Co—Cr—Mo alloy or 316 stainless steel. The installation manner can be like sticking shown in FIG. 3 (a gap is kept between the first side wall 33 and the outer sidewall of the pad 3) or completely attaching to the outer sidewall of the pad 3 shown in FIG. 6A, or inserting two ends of the first side wall 33 into the position holes (or position notches) on the outer sidewall of the pad 3, but it is not limited thereto. The first side wall 33 may completely or incompletely circle the outer sidewall of the pad 3, too. Similarly, for the implanted tibial component 1 to be tightly clutched by the tissue at the patient's implanted portion and act with the patient's knee for better postoperative stability, as shown in FIG. 6A, each of the two opposite outer sidewalls of the tibial component 1 further has a second side wall 17. Or the second side wall 17 completely or incompletely circles the outer sidewall of the tibial component 1. The second side wall 17 has a plurality of second through holes. The dimension, disposing manner and material of the second side wall 17 is the same or similar with those on the first side wall 33 on the outer sidewall of the pad 3, so they are not repeated here.

Moreover, to easily observe the abrasion of the pad 3 after the operation, an abrasion meter 32 may be disposed on the front portion of the pad 3. The abrasion meter 32 may be like ladder as shown in the figure and it is made of metal material directly scribed on the outer sidewall at the front portion of the pad 3. Or it may be a metal line buried near the front portion of the pad 3. Therefore, the surgeon can directly use X-ray imaging to obtain radiography showing the patient's knee where the knee joint prosthesis K is implanted. By observing the abrasion meter 32 shown on the radiography, the degree of the pad 3 being abraded by the femoral component 2 can be estimated.

In a preferable example, the top surface 11 of the tibial component 1 looks like a concave surface, and the depth at the middle is deeper than that at the front or the rear. Thus, the pad 3 is easy to engage and assemble with the tibial component 1 by slide-in during surgery, but it is not limited thereto. Namely, in other embodiments, the pad 3 can be directly formed on the top surface 11 of the tibial component 1 when manufacturing by wrapping injection or insert injection, so it is not necessary to engage the first engagement portion 31 of the pad 3 with the second engagement portion 16 of the tibial component 1. Alternatively, in the factory, the pad 3 has been engaged with the top surface 11 of the tibial component 1. Alternatively, the pad 3 and the tibial component 1 are isolated from each other, and the pad 3 is engaged with the tibial component 1 until performing surgery.

Figure 6B:
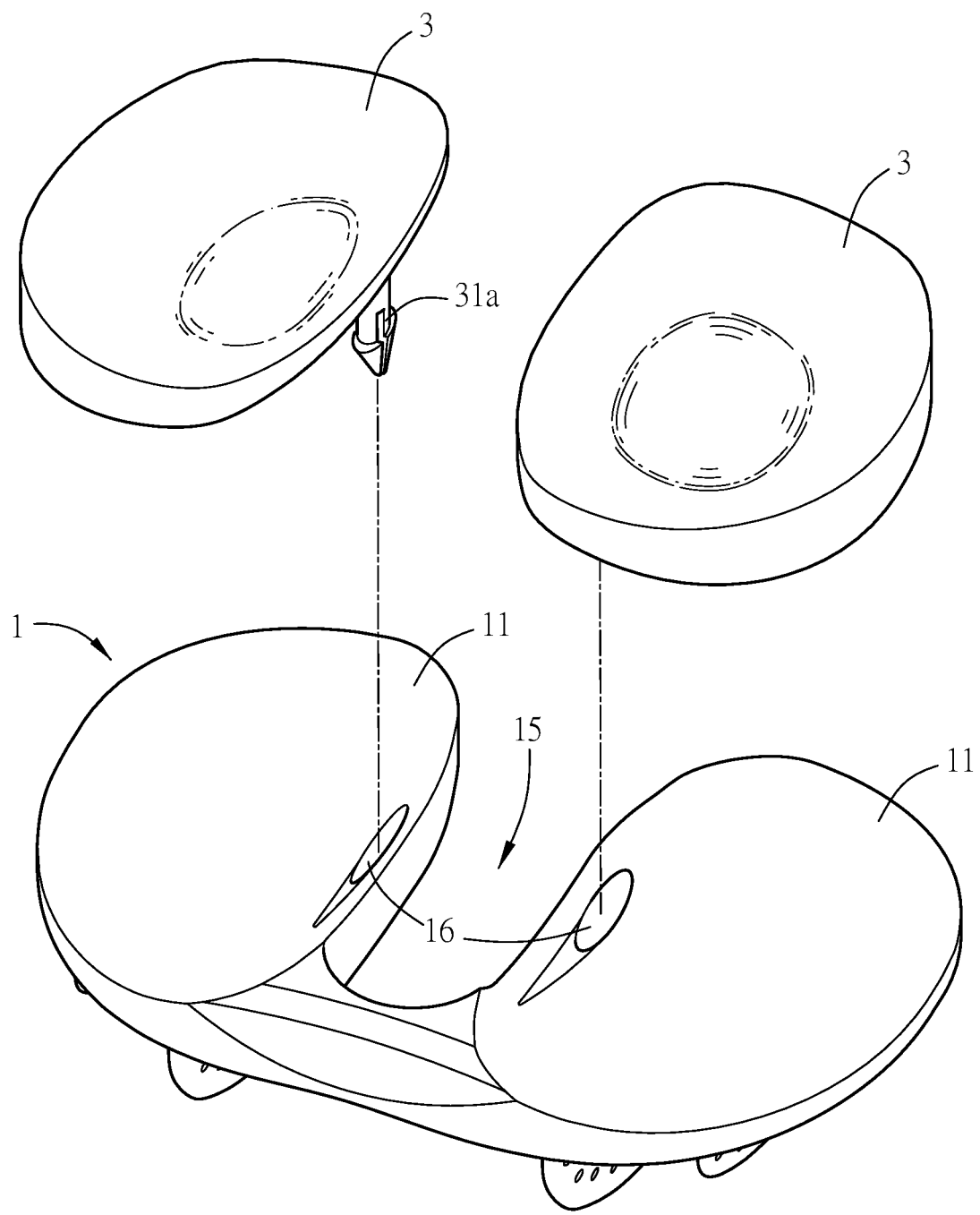
Figure 6C:
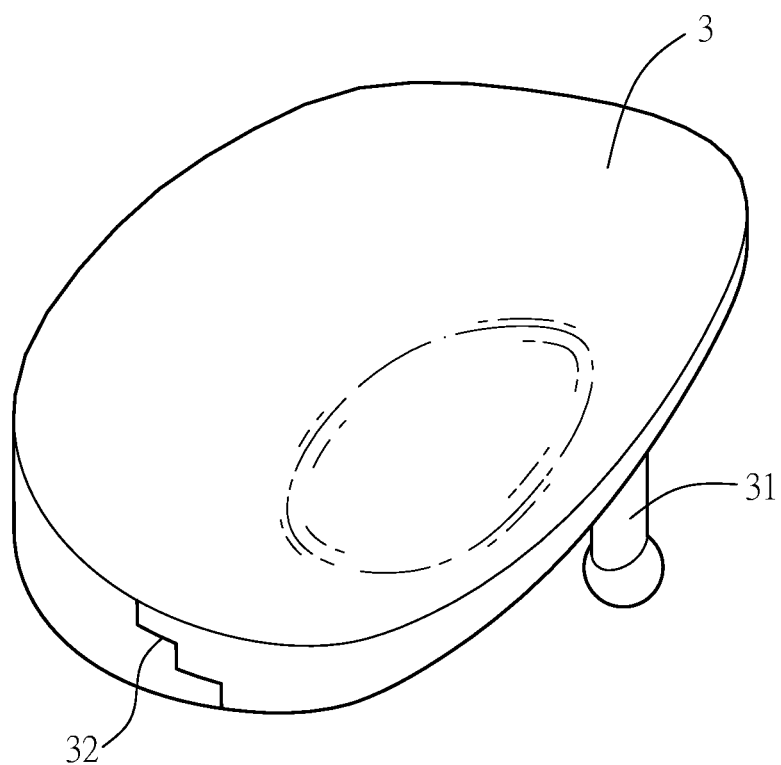

In a preferable example, as shown in FIG. 6B, the top surface 11 of the tibial component 1 can be a shallow-dish concave mentioned above, the second engagement portion 16 of the tibial component 1 can extend from the first portion 1a and the second portion 1b close to the front of the tibial component 1 to the middle section and look like a concave groove. Only the middle section close to the first slot 15 is through-hole conformation so that the pad 3 is easy to assemble by slide-in along the direction along front-to-rear of the tibial component 1 during surgery. The first engagement portion 31a of the pad 3 firstly contacts the concave groove of the second engagement portion 16 of the tibial component 1 and is thus limited. When the pad 3 continues to slide into, the first engagement portion 31a of the pad 3 slides to and penetrate a part of the through hole of the second engagement portion 16 of the tibial component 1 so as to complete the engagement assembly of the pad 3 with the tibial component 1.

Besides, referring to FIG. 6A, in a preferable example, the tibial component 1 can have no connection portion 1c. Namely, the first portion 1a and the second portion 1b of the tibial component 1 are independently disposed and individually implanted into the corresponding tibial plateau during implanting.

Besides, a tibial component 1 is also provided, and it is similar to the tibial component 1 of the knee joint prosthesis K mentioned above. The tibial component 1 includes the top surface 11, the bottom surface 12 opposite to the top surface 11 and the first slot 15. The first slot 15 passes through the top surface 11 and the bottom surface 12 to accommodate the anterior cruciate ligament ACL and the posterior cruciate ligament PCL. The tibial component 1 has at least one the first protrusion 13 disposed on the bottom surface 12. Each of the first protrusion 13 has at least one first through hole 14. Because composition, variation or connection relationship to other elements of each detail elements of the tibial component 1 can refer to the previous embodiments, they are not repeated here.

Besides, a femoral component 2 is also provided. It is similar to the femoral component 2 of the knee joint prosthesis K mentioned above. Similarly, the femoral component 2 is disposed corresponding to the tibial component 1. The top surface 11 of the tibial component 1 carries the femoral component 2. The femoral component 2 includes the second slot 25 which is adapted to accommodate the anterior cruciate ligament ACL and the posterior cruciate ligament PCL. The femoral component 2 has at least one second protrusion 23 disposed on the surface 21 against the tibial component 1. Each of the second protrusion 23 has at least one second through hole 24. Because composition, variation or connection relationship to other elements of each detail elements of the femoral component 2 can refer to the previous embodiments, they are not repeated here.

Figure 7A:
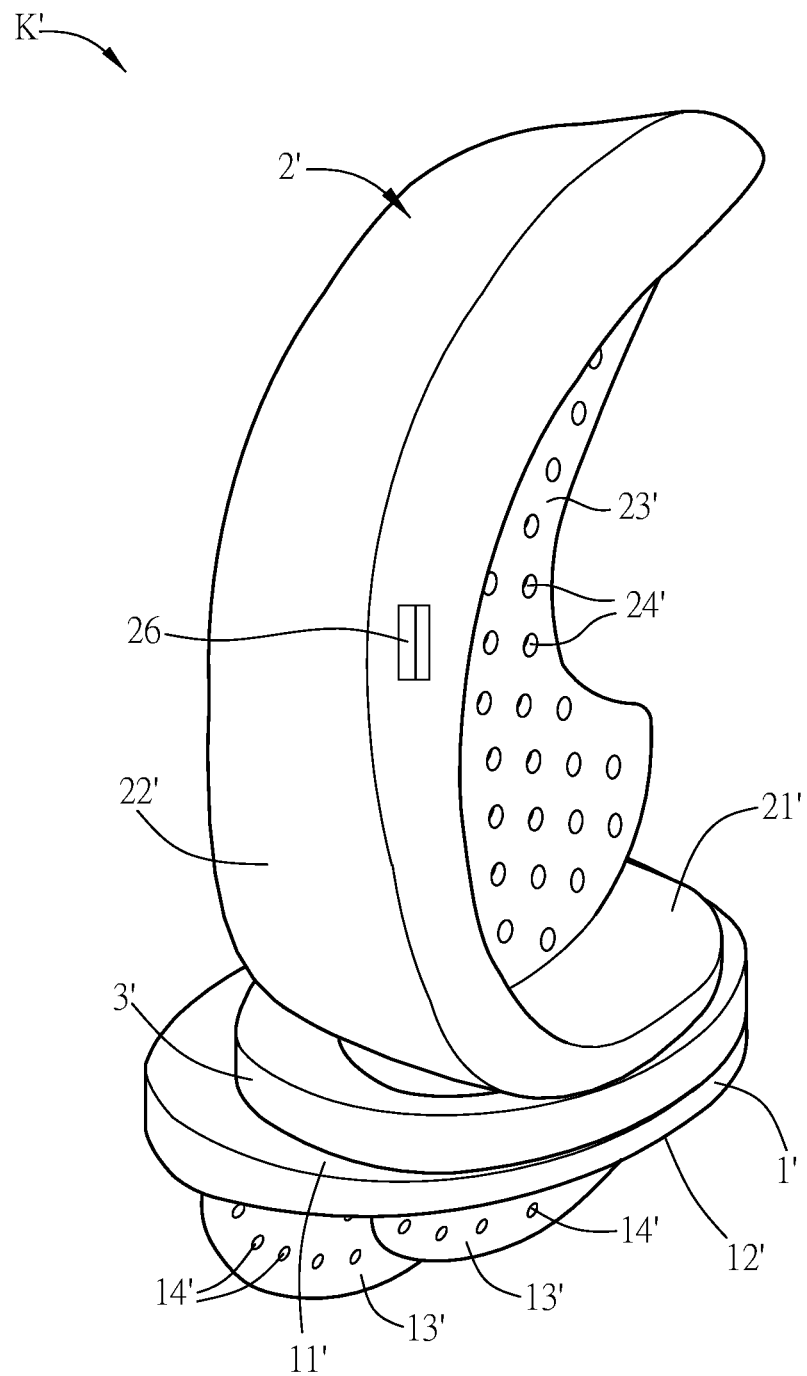
FIG. 7A to FIG. 7B are schematic diagrams showing the assembly of the knee joint prosthesis according to another embodiment.
Figure 7B:
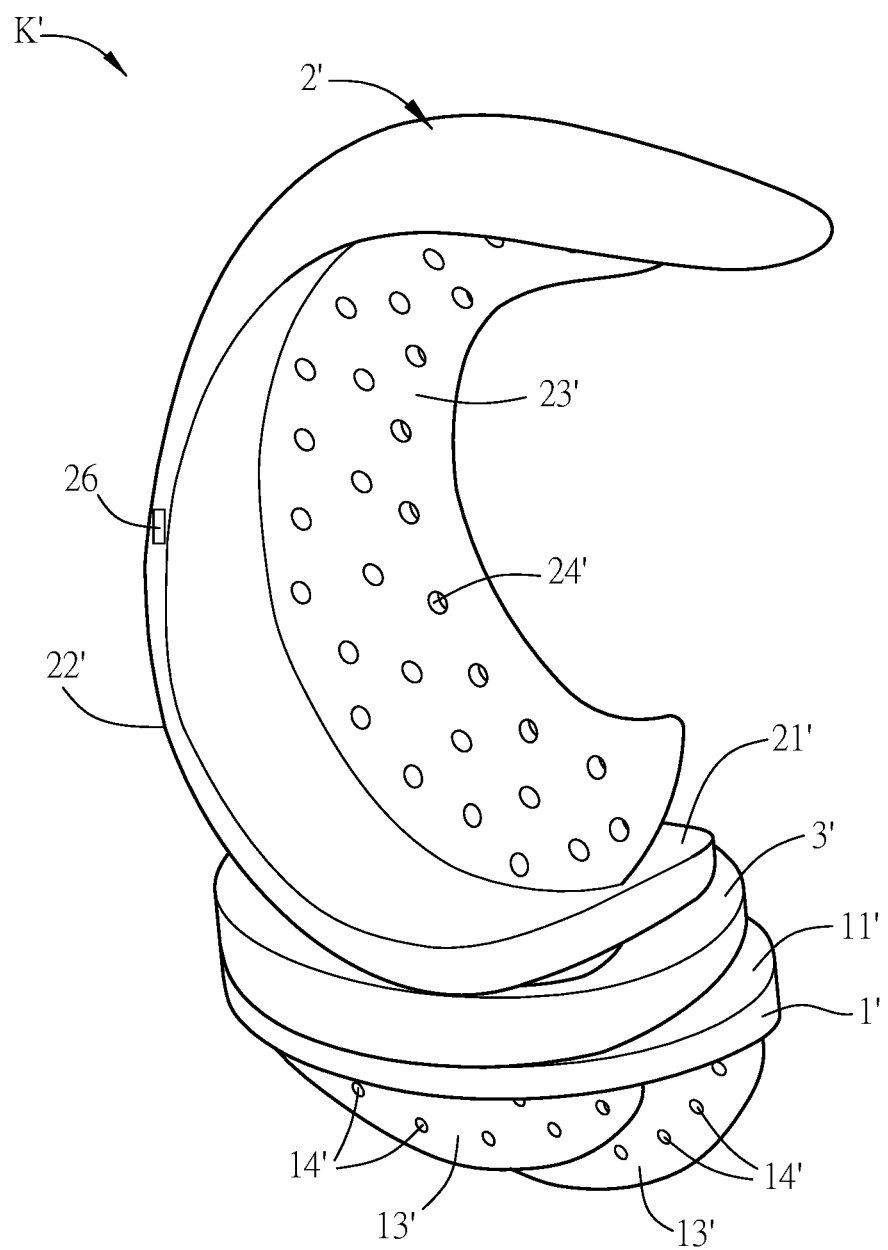

Besides, another knee joint prosthesis K' is also provided, and it is suitable to unicompartmental knee arthroplasty. Referring to FIG. 7A and FIG. 7B, they are schematic diagrams showing the assembly of the knee joint prosthesis according to another embodiment. The knee joint prosthesis K' includes a tibial component 1' and a femoral component 2'. As shown in the figures, the knee joint prosthesis K' of the embodiment is suitable to unicompartmental knee arthroplasty, so compared with the femoral component 2 and the tibial component 1 mentioned in the previous embodiments, the tibial component 1' and the femoral component 2' both only have conformations corresponding to the femur unicondylar and the tibia unicondylar. As to the correspondence to the medial condyle portion or the lateral condyle portion, it is not limited. The person skilled in the art should understand that the knee joint prosthesis K' in the embodiment needs corresponding modification of detail conformation when applied to the medial condyle portion or the lateral condyle portion according to the figures and the description. The tibial component 1' includes a top surface 11' and a bottom surface 12' opposite the top surface 11'. The tibial component 1' has at least one first protrusion 13' disposed on the bottom surface 12'. In the embodiment, a plurality of the first protrusions 13' are disposed for example. Each of the first protrusions 13' has at least one first through hole 14'. In the embodiment, a plurality of the first through holes 14' are disposed for example. The femoral component 2' roughly looks like an arc and is disposed corresponding to the tibial component 1'. The top surface 11' of the tibial component 1' carries the femoral component 2' (the surface 22' of the femoral component 2' which faces the tibial component 1' directly abuts the top surface 11' of the tibial component 1', or alternatively the pad 3' is utilized to buffer so the femoral component 2' is supported on the top surface 11' of the tibial component 1' and the surface 22' of the femoral component 2' facing the tibial component 1' does not directly contact the top surface 11' of the tibial component 1' by indirect carrying manner). The femoral component 2' is slidably disposed on the tibial component 1'. After the tibial component 1' is implanted into the tibial plateau of the patient, the first protrusion 13' is inserted into the tibial plateau.

As to such the tibial component 1' adapted for unicompartmental knee arthroplasty, it matches the structure of tibia unicondylar. Its front portion is thicker than the front portion of the tibial component 1 for tibia bicondylar for total keen joint replacement. Therefore, although the position block 41 of the auxiliary implantation device 4 can not be used, the abuting wall 434 of the wrench 43 can directly abut the thicker front portion of the tibial component 1', the lock end 431 of the wrench 43 squeezes the top surface 11' of the tibial component 1', and similarly the rear portion of the first protrusion 13' of the tibial component 1' abuts the patient's tibial plateau. The surgeon can take the place of the patient's tibial plateau abutted by the first protrusion 13' as the fulcrum, and the first protrusion 13' of the tibial component 1' can also slide into the patient's tibial plateau.

The femoral component 2' has at least one second protrusion 23' disposed on the surface 21' against the tibial component 1'. In the embodiment, one second protrusion 23' is disposed for example. The second protrusion 23' has at least one second through hole 24'. In the embodiment, a plurality of the second through holes 24' are disposed for example. After the femoral component 2' is implanted into the patient's knee, the second protrusion 23' is inserted into the corresponding femoral condyles.

In the embodiment, the tibial component 1' and the femoral component 2' of the knee joint prosthesis K' and the pad 3' used together vary correspondingly for applied to unicompartmental knee arthroplasty. Because composition, detail variation or connection relationship to other elements of other elements can refer to the previous embodiments, they are not repeated here.

Besides, another tibial component 1' is also provided. It is similar to the tibial component 1' of the knee joint prosthesis K'. The tibial component 1' includes the top surface 11' and the bottom surface 12' opposite the top surface 11'. The tibial component 1' has at least one first protrusion 13' disposed on the bottom surface 12'. Each of the first protrusion 13' has at least one first through hole 14'. Because composition, variation or connection relationship to other elements of each detail elements of the tibial component 1' can refer to the previous embodiments, they are not repeated here.

Besides, another femoral component 2' is also provided, it is similar to the femoral component 2' of the knee joint prosthesis K' mentioned above. The femoral component 2' is disposed corresponding to the tibial component 1', and the femoral component 2' has at least one the second protrusion 23' disposed on the surface 21' against the tibial component 1', and each of the second protrusion 23' has at least one second through hole 24'. Because composition, variation or connection relationship to other elements of each detail elements of the femoral component 2' can refer to the previous embodiments, they are not repeated here.

As mentioned above, as to the knee joint prosthesis, the tibial component and the femoral component thereof, because the tibial component and the femoral component respectively have at least one first protrusion and the second protrusion, and the first protrusion and the second protrusion respectively have at least one first through hole and at least one second through hole. After the tibial component and the femoral component are respectively implanted into the tibial plateau and the femoral condyles, the first protrusion is inserted into the tibial plateau and the second protrusion is inserted into the femoral condyles. The bone trabeculae in postoperative healing process will grow to pass through the first through hole and the second through hole so as to fix the tibial component and the femoral component to the implanted portion. Moreover, if the knee joint prosthesis is needed to replace in the future, the bone trabeculae can grow in the first through hole and the second through hole to fix the replaced tibial component or femoral component.

In addition to the above effect of the knee joint prosthesis and the tibial component and the femoral component thereof, in one embodiment, because the tibial component and the femoral component respectively have the first slot and the second slot disposed corresponding to each other for accommodating the cruciate ligament of the patient's knee, the orthopedic surgeons can adopt cruciate ligament-retaining to keep the stability of the postoperative joint and reduce the wear of the new joint when performs total keen joint replacement.

Although the invention has been described with reference to specific embodiments, this description is not meant to be construed in a limiting sense. Various modifications of the disclosed embodiments, as well as alternative embodiments, will be apparent to persons skilled in the art. It is, therefore, contemplated that the appended claims will cover all modifications that fall within the true scope of the invention.

What is claimed is:

1. A knee joint prosthesis, comprising:
a tibial component, including a top surface, a bottom surface opposite to the top surface and a first slot passing through the top surface and the bottom surface for accommodating a cruciate ligament, wherein the tibial component includes at least one first protrusion disposed on the bottom surface, and the at least one first protrusion includes a plurality of first through holes; and
a femoral component, carried by the tibial component and including a second slot for accommodating the cruciate ligament, wherein the femoral component includes at least one second protrusion disposed on a surface thereof opposite to the tibial component, and the at least one second protrusion includes a plurality of second through holes,
wherein the at least one first protrusion gradually becomes thinner along an extending direction away from the bottom surface, and a longitudinal direction of the at least one first protrusion is substantially perpendicular to a medial-lateral direction of the tibial component,
wherein the at least one first protrusion includes a rear portion corresponding to a posterior of the tibial component and a front portion corresponding to an anterior of the tibial component, and a length of the rear portion along the extending direction away from the bottom surface is greater than a length of the front portion along the extending direction away from the bottom surface,
wherein the at least one first protrusion has a thickest part where the at least one first protrusion directly connects to the bottom surface, and
wherein the at least one first protrusion further includes a receded incision positioned on a rear edge of the at least one first protrusion and the receded incision is receded in a direction from posterior to anterior.

2. The knee joint prosthesis of claim 1, wherein the tibial component further includes at least one second through hole passing through the top surface and the bottom surface and located away from the at least one first protrusion.

3. The knee joint prosthesis of claim 1, wherein the tibial component further includes at least one engagement portion adjacent to the first slot.

4. The knee joint prosthesis of claim 1, wherein the tibial component further includes at least one first sidewall and an engagement groove, wherein the at least one first sidewall surrounds the first slot and the engagement groove is disposed on the at least one first sidewall.

5. The knee joint prosthesis of claim 1, wherein the tibial component further includes a second sidewall having a plurality of first apertures.

6. The knee joint prosthesis of claim 1, wherein the plurality of first through holes are distributed from sparse to dense along the extending direction.

7. The knee joint prosthesis of claim 1, wherein the femoral component further includes at least two holding notches respectively located at two sides thereof.

8. The knee joint prosthesis of claim 1, wherein the at least one second protrusion further includes a second cutting edge and a second base, the second base is disposed between the second cutting edge and a surface of the femoral component opposite to the tibial component.

9. The knee joint prosthesis of claim 1, wherein the at least one second protrusion further includes at least one position pillar disposed on a middle segment thereof.

10. The knee joint prosthesis of claim 1, further comprising at least one pad located between the tibial component and the femoral component.

11. The knee joint prosthesis of claim 10, wherein the at least one pad includes a third sidewall having a plurality of second apertures.

12. The knee joint prosthesis of claim 11, wherein the at least one pad further includes an abrasion meter.

13. A tibial component, comprising:
a top surface, a bottom surface opposite to the top surface, and a slot passing through the top surface and the bottom surface for accommodating a cruciate ligament,
wherein the tibial component includes at least one first protrusion disposed on the bottom surface and the at least one first protrusion includes a plurality of first through holes,
wherein the at least one first protrusion gradually becomes thinner along an extending direction away from the bottom surface, and a longitudinal direction of the at least one first protrusion is substantially perpendicular to a medial-lateral direction of the tibial component,
wherein the at least one first protrusion includes a rear portion corresponding to a posterior of the tibial component and a front portion corresponding to an anterior of the tibial component, and a length of the rear portion along the extending direction away from the bottom surface is greater than a length of the front portion along the extending direction away from the bottom surface,
wherein the at least one first protrusion has a thickest part where the at least one first protrusion directly connects to the bottom surface, and
wherein the at least one first protrusion further includes a receded incision positioned on a rear edge of the at least one first protrusion and the receded incision is receded in a direction from posterior to anterior.

14. The tibial component of claim 13, further comprising at least one second through hole passing through the top surface and the bottom surface and located away from the at least one first protrusion.

15. The tibial component of claim 13, further comprising at least one engagement portion adjacent to the slot.

16. The tibial component of claim 13, further comprising at least one first sidewall and an engagement groove, wherein the at least one first sidewall surrounds the slot and the engagement groove is disposed on the at least one first sidewall.

17. The tibial component of claim 13, further comprising a second sidewall having a plurality of first apertures.

18. The tibial component of claim 13, wherein the plurality of first through holes are distributed from sparse to dense along the extending direction.

* * * * *